(12) United States Patent
Panicker et al.

(10) Patent No.: US 10,287,282 B2
(45) Date of Patent: May 14, 2019

(54) METHODS AND AGENTS FOR TREATING DISEASE

(71) Applicant: ANGION BIOMEDICA CORP., Uniondale, NY (US)

(72) Inventors: Bijoy Panicker, Holtsville, NY (US); Lambertus J. W. M. Oehlen, Westbury, NY (US)

(73) Assignee: ANGION BIOMEDICA CORP., Uniondale, NY (US)

( * ) Notice: Subject to any disclaimer, the term of this patent is extended or adjusted under 35 U.S.C. 154(b) by 0 days.

(21) Appl. No.: 15/540,592

(22) PCT Filed: Dec. 29, 2015

(86) PCT No.: PCT/US2015/067801
§ 371 (c)(1),
(2) Date: Jun. 29, 2017

(87) PCT Pub. No.: WO2016/109492
PCT Pub. Date: Jul. 7, 2016

(65) Prior Publication Data
US 2018/0002324 A1 Jan. 4, 2018

Related U.S. Application Data

(60) Provisional application No. 62/099,120, filed on Dec. 31, 2014.

(51) Int. Cl.
| C07D 417/06 | (2006.01) |
| A61K 31/427 | (2006.01) |
| A61K 31/4439 | (2006.01) |
| C07D 417/14 | (2006.01) |

(52) U.S. Cl.
CPC .......... *C07D 417/06* (2013.01); *A61K 31/427* (2013.01); *A61K 31/4439* (2013.01); *C07D 417/14* (2013.01)

(58) Field of Classification Search
CPC .................................................. C07D 417/06
USPC ...................................... 546/270.1; 514/338
See application file for complete search history.

(56) References Cited

U.S. PATENT DOCUMENTS

| 4,818,765 A | 4/1989 | Weith et al. |
| 5,292,758 A | 3/1994 | Yoshino et al. |
| 5,308,854 A | 5/1994 | Hoffman, Jr. et al. |
| 5,376,669 A | 12/1994 | Lang et al. |
| 5,389,614 A | 2/1995 | Konig et al. |
| 5,616,537 A | 4/1997 | Yokota et al. |
| 5,891,916 A | 4/1999 | Kato et al. |
| 5,925,645 A | 7/1999 | Schmidt et al. |
| 5,977,101 A | 11/1999 | Ali et al. |
| 6,020,339 A | 2/2000 | Perrier et al. |
| 6,818,635 B2 | 11/2004 | Nelson et al. |
| 7,115,608 B2 | 10/2006 | Guillemont et al. |
| 7,153,960 B2 | 12/2006 | Zhou et al. |
| 7,262,318 B2 | 8/2007 | Hamanaka et al. |
| 7,282,591 B2 | 10/2007 | Ali et al. |
| 7,579,348 B2 | 8/2009 | Wang et al. |
| 7,625,915 B2 | 12/2009 | Dumas et al. |
| 8,039,500 B2 | 10/2011 | Aso et al. |
| 8,124,625 B2 | 2/2012 | Yamamori et al. |
| 8,218,718 B1 | 7/2012 | Van Herk et al. |
| 8,404,856 B2 | 3/2013 | Tucker et al. |
| 8,541,424 B2 | 9/2013 | DeGoey et al. |
| 2002/0045615 A1 | 4/2002 | Alanine et al. |
| 2003/0166668 A1 | 9/2003 | Zandt et al. |
| 2003/0199523 A1 | 10/2003 | Snutch |
| 2005/0288340 A1 | 12/2005 | Hamanaka |
| 2006/0025474 A1 | 2/2006 | Wallace et al. |
| 2006/0106020 A1 | 5/2006 | Rodgers |
| 2007/0173527 A1 | 7/2007 | Bressi et al. |
| 2007/0244120 A1 | 10/2007 | Dumas et al. |
| 2008/0300281 A1 | 2/2008 | Dumas et al. |
| 2008/0221078 A1 | 9/2008 | Black et al. |
| 2009/0018124 A1 | 1/2009 | Kim et al. |
| 2009/0192190 A1 | 7/2009 | Gyback et al. |
| 2010/0041891 A1 | 2/2010 | Setoh et al. |
| 2010/0168104 A1 | 7/2010 | Guillemont et al. |
| 2012/0046290 A1 | 2/2012 | Dumas et al. |
| 2013/0023502 A1 | 1/2013 | Dahmann et al. |
| 2013/0137728 A1 | 5/2013 | Beeson et al. |
| 2013/0196967 A1 | 8/2013 | Bartolozzi et al. |

(Continued)

FOREIGN PATENT DOCUMENTS

| AU | 2006201959 | 6/2006 |
| CN | 101041660 | 9/2007 |

(Continued)

OTHER PUBLICATIONS

Ivanisevic et al. "Use of X-ray . . . " Pharm. Sci. Encycl. p. 1-42 (2010).*

(Continued)

*Primary Examiner* — Patricia L Morris
(74) *Attorney, Agent, or Firm* — Mark S. Cohen; Pearl Cohen Zedek Latzer Baratz LLP

(57) ABSTRACT

The present invention provides compounds having the general structural formula (I) [formula should be inserted here] and pharmaceutically acceptable derivatives thereof, as described generally and in classes and subclasses herein, and additionally provides pharmaceutical compositions thereof, and methods for the use thereof for the treatment of any of a number of conditions or diseases involving elevated levels of aldosterone or abnormal or excessive fibrosis, such as kidney disease and hypertension.

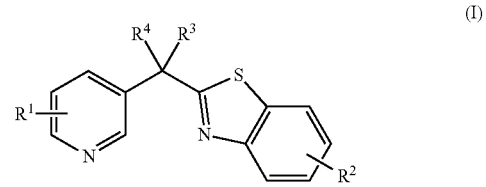

(I)

11 Claims, 6 Drawing Sheets

(56) References Cited

U.S. PATENT DOCUMENTS

| | | |
|---|---|---|
| 2013/0210859 A1 | 8/2013 | Kobayashi et al. |
| 2014/0018401 A1 | 1/2014 | Panicker et al. |
| 2014/0107094 A1 | 4/2014 | Leonard et al. |
| 2014/0107096 A1 | 4/2014 | Leonard et al. |
| 2014/0107097 A1 | 4/2014 | Leonard et al. |

FOREIGN PATENT DOCUMENTS

| | | |
|---|---|---|
| CN | 102206172 | 10/2011 |
| EA | 201100037 A1 | 8/2011 |
| EP | 299620 | 1/1989 |
| EP | 639573 | 2/1995 |
| EP | 668270 | 8/1995 |
| EP | 0796846 | 9/1997 |
| JP | S46-31862 | 9/1971 |
| JP | 06016638 | 1/1994 |
| JP | 1017549 | 1/1998 |
| WO | WO 1998004528 | 2/1998 |
| WO | WO 1999032106 | 7/1999 |
| WO | WO 1999032111 | 7/1999 |
| WO | WO 1999059586 | 11/1999 |
| WO | WO 2005/105814 | 11/2005 |
| WO | WO 2007091140 | 8/2007 |
| WO | WO 2008017827 | 2/2008 |
| WO | WO 2009081246 | 7/2009 |
| WO | WO 2011097946 | 8/2011 |
| WO | WO 2011117254 | 9/2011 |
| WO | WO 2012111142 | 8/2012 |
| WO | WO 2013019653 | 2/2013 |
| WO | WO 2013019682 | 2/2013 |
| WO | WO 2013043518 | 3/2013 |
| WO | WO 2013151876 | 10/2013 |
| WO | WO 2013181104 | 12/2013 |
| WO | WO 2014055595 | 4/2014 |

OTHER PUBLICATIONS

Seddon "Pseudopolymorph . . . " Crystal Growth & design v.4(6) p. 1087 (2004) (2 pages from internet).*
Jain et al., "Polymorphism in Pharmacy", Indian Drugs, 1986, 23(6) 315-329.*
Wolff, ed., Burger's Medicinal Chemistry and Drug Discovery, 5th edition, NY: John Wiley & Sons, 1996, vol. 1, pp. 949-976.*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory & Morris (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Braga et al., "Making crystals from . . . " J. Royal Soc. Chem. Commun. p. 3635-3645 (2005).*
Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Bundgaard, Design of Prodrugs, Chapter 1, p. 1, 1985.*
Silverman, Prodrugs and Drug Delivery Systems, The Organic Chemistry of Drug Design and Drug Action, Chapter 8, pp. 352-400, 1992.*
Banker et al., Prodrugs, Modern Pharmaceutics, 3rd edition, Revised and Expanded, pp. 451 and 596, 1986.*
Extended European Search Report, dated Jun. 13, 2018, from corresponding European Patent Application No. 15876137.9.

* cited by examiner

Figure 4
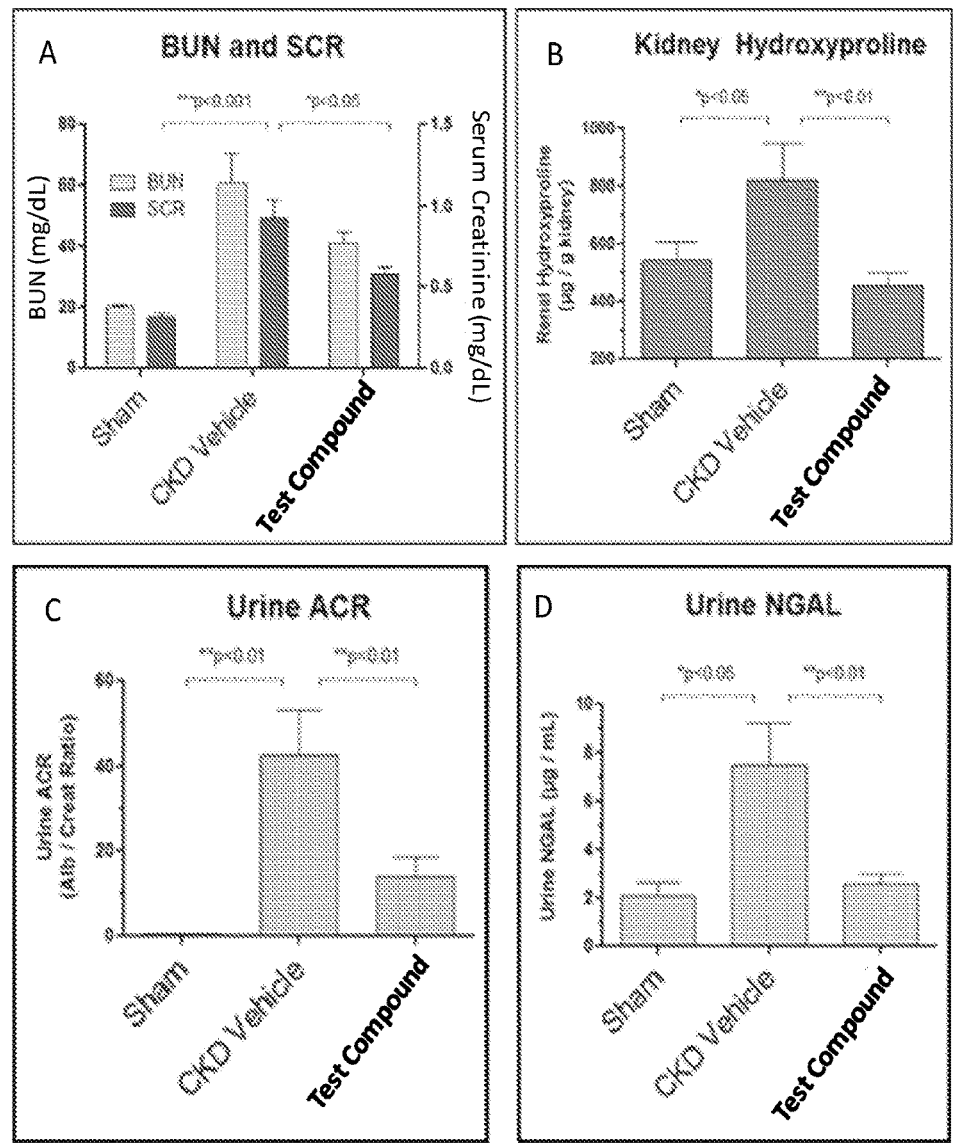
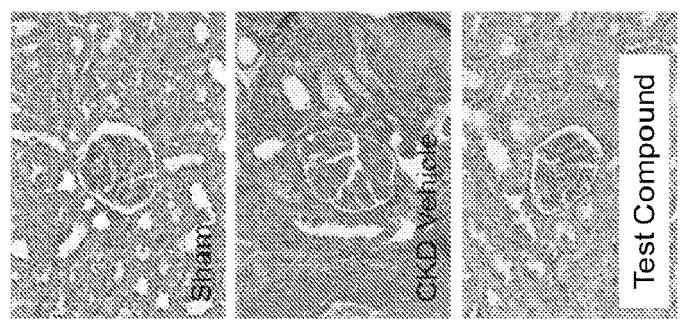
Figure 5

METHODS AND AGENTS FOR TREATING DISEASE

GOVERNMENT SUPPORT

This invention was made with government support under DK095625 awarded by the National Institutes of Health. The government has certain rights in the invention.

BACKGROUND OF THE INVENTION

The renin-angiotensin-aldosterone system (RAAS) plays a critical role in renal physiology. Inhibitors of angiotensin-converting enzyme (ACE) or angiotensin receptor blockers (ARB) are the mainstay in the clinical management of hypertension and renal disorders such as CKD. These treatments are thought to work in large part by reducing aldosterone levels. Despite initial success of ACE inhibition or ARB therapy to reduce aldosterone, in 30-40% of patients, aldosterone is eventually found to return to pretreatment levels, thus severely limiting the long term therapeutic effectiveness. The clinical significance of this "aldosterone breakthrough" is increasingly recognized and several approaches to combat aldosterone escape are being considered. The mineralocorticoid aldosterone has long been known as a key hormone that regulates electrolyte homeostasis, fluid volume and blood pressure. Aldosterone acts through the mineralocorticoid receptor (MR) in the distal nephrons of the kidney to control sodium re-absorption and potassium excretion. In patients with chronic renal disease, plasma aldosterone levels are usually found to be elevated and to correlate with proteinuria. Aldosterone is thought to directly accelerate renal damage by sustaining cell growth, inflammation and fibrosis.

One in ten American adults have some level of chronic kidney disease (CKD), which amounts to more than 20 million US citizens. CKD occurs in both diabetic and non-diabetic nephropathies and is characterized by increasing proteinuria, declining functional nephron mass and a concomitant decline in renal function (glomerular filtration rate (GRF)<60 ml/min). It is estimated that 20-40% of diabetes patients progress to some form of CKD. In 2004, approximately 8 million people in the US were diagnosed with a glomerular filtration rate <60 ml/min. CKD often transitions to end-stage renal disease, a life-threatening condition requiring renal replacement therapy. The number of patients reaching end-stage renal disease has been increasing at an average of 7% per year over the last 10 years. Worldwide, approximately 1.1 million patients are on renal replacement therapy and this number is expected to exceed 2 million in 10 years, with 0.5 million from the US. Many people will die as a result of renal failure if renal replacement therapy is not provided. The annual mortality rate is 20% for patients on dialysis who are waiting for renal transplantation. The combined cost of dialysis and kidney transplantation is estimated to exceed $1 trillion. At present, there is no treatment reverses the course of CKD. Many patients with kidney disease benefit from antihypertensive therapy with inhibitors of angiotensin converting enzyme (ACE) or angiotensin receptor blockers (ARBs). These drugs are usually given in concert with diuretics. However, despite initial success of ACE inhibition or ARB therapy, their long term therapeutic effectiveness is often limited. There continues to be a great unmet medical need for therapies that can complement the current pharmaceutical armamentarium by slowing disease progression, reversing symptoms and delaying or preventing the need for renal replacement therapy. There is also a need for compounds that can prevent the development of fibrosis.

SUMMARY OF THE INVENTION

In one embodiment, certain novel inventive compounds have the structure shown in Formula (I) below:

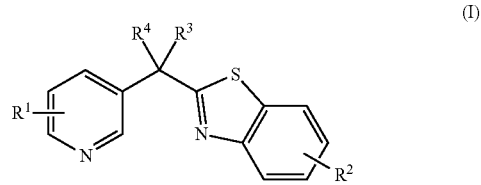

or a salt, solvate, enantiomer, ester, or hydrate thereof;
wherein $R^1$ and $R^2$ are each independently one or more H, halogen, haloalkyl, $NO_2$, CN, $COOR^5$, $SO_2R^5$, $CONR^5R^6$, $SO_2NR^5R^6$, $NR^5R^6$, $OR^5$, alkyl, alkenyl, alkynyl, heteroalkyl, aryl or hetero aryl, any of which is further substituted by one or more $R^7$; or two $R^2$ substituents taken together with the respective carbon atom to which they are attached, form a 5-6 membered heterocyclic ring, wherein said ring is optionally substituted with one or more $R^7$;
$R^3$ is H, alkyl, alkenyl or alkynyl, any of which is further substituted by one or more $R^7$;
$R^4$ is H, $NR^5R^6$, $SR^5$, or $OR^5$;
$R^5$ and $R^6$ are independently hydrogen, alkyl, aryl, heteroaryl or haloalkyl;
$R^7$ is H, halogen, alkyl, haloalkyl, $NO_2$, CN, $COOR^8$, $SO_2R^8$, $CONR^8R^9$, $SO_2NR^8R^9$, $NR^8R^9$, or $OR^8$; and
$R^8$ and $R^9$ are independently hydrogen, alkyl or haloalkyl.
In certain embodiments, $R^1$ is methoxy, ethyloxy, 1-propyloxy or 2-propyloxy. In certain embodiments, $R^2$ is trifluoromethoxy or methylenedioxy optionally further substituted with difluoro.

In another embodiment, a pharmaceutical composition is provided comprising a compound of Formula I and a diluent, excipient, carrier, or one or more other components to facilitate the administration of a compound embodied here to a subject in need thereof.

In one embodiment, compounds of the invention inhibit aldosterone synthase. In one embodiment, compounds of the invention inhibit CYP11B2. In another embodiment, compounds of the invention selectively inhibit CYP11B2 compared to CYP11B1.

In another aspect, the present invention is directed to a method of prevention, treatment or lessening of the severity of a condition or disease associated with or characterized by increased or elevated aldosterone levels, comprising administering to a subject in need thereof an effective amount of a compound of Formula I or a pharmaceutical composition thereof.

In another aspect, the present invention is directed to a method of prevention, treatment or lessening of the severity of a condition or disease associated with or characterized by increased fibrosis, comprising administering to a subject in need thereof an effective amount of a compound of Formula I or a pharmaceutical composition thereof.

In certain embodiments, the diseases and conditions benefited by treatment with an effective amount of a compound mentioned above or pharmaceutical composition thereof include but are not limited to chronic renal disease and hypertension. Other conditions related to elevated aldosterone levels, or hyperaldosteronism, include hypertensive vascular complications (hypertrophy followed by sclerosis of intimal smooth muscle), renal complications (sclerosis), and cardiac complications (hypertrophy followed by dilatation). Symptoms of elevated aldosterone levels treatable by the compounds, compositions and methods herein include fatigue, headache, hypokalemia, hypernatraemia, hypomagnesemia, intermittent or temporary paralysis, muscle spasms, muscle weakness, numbness, polyuria, polydipsia, tingling, and metabolic alkalosis, by way of non-limiting examples.

In certain embodiments, the diseases and conditions benefited by treatment with an effective amount of a compound mentioned above or pharmaceutical composition thereof include but are not limited to fibrotic liver disease, hepatic ischemia-reperfusion injury, cerebral infarction, ischemic heart disease, cardiac fibrosis, renal disease or lung (pulmonary) fibrosis. In other embodiments, the disease or condition is liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; pancreatitis; renal failure; renal fibrosis; chronic kidney disease; polycystic kidney disease; scleroderma; systemic sclerosis; dermal fibrosis and idiopathic pulmonary fibrosis. In still further embodiments, the treatment is for wounds for acceleration of healing; reducing post-surgical scarring; reducing adhesion formation; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; muscular dystrophy, amyotrophic lateral sclerosis, and/or diabetes mellitus.

Definitions

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbanked, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; aralkyl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$ SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons as defined by IUPAC, which are optionally substituted with one or more functional groups. As defined herein, "aliphatic" is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms. In some instances aliphatic can include alicyclic or cycloalkyl, including unsaturations therein.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds that combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norbornyl moieties and the like, which again, may bear one or more substituents.

The term "cycloalkyl", as used herein, refers to cyclic alkyl groups, specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like. Additional examples of generally applicable substituents are illustrated by the specific embodiments shown in the Examples that are described herein.

The term "heteroaliphatic", as used herein, refers to aliphatic moieties in which one or more carbon atoms in the main chain have been replaced with a heteroatom. Thus, a heteroaliphatic group refers to an aliphatic chain which contains one or more oxygen, sulfur, nitrogen, phosphorus or silicon atoms in place of carbon atoms in the aliphatic main chain. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$-, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$— or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more hydrogen atoms thereon with aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$), —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic". Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring having p-orbitals perpendicular to the plane of the ring at each ring atom, and satisfying the Huckel rule where the number of pi electrons in the ring is (4n+2) wherein n is an integer. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic) aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(alkyl)heteroaromatic, and -(heteroalkyl)heteroaromatic" are interchangeable. In some instances corresponding moieties may be referred to synonymously as aralkyl, heteroaralkyl and the like. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As defined herein, "aryl" and "heteroaryl" groups (including bicyclic aryl groups) can be unsubstituted or substituted, wherein substitution includes replacement of one or more of the hydrogen atoms thereon independently with any of the previously mentioned substituents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O) $NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure $NH_2R'$—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O) N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, i so-propyl amino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "C$_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-alkyl and N-aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

BRIEF DESCRIPTIONS OF THE FIGURES

FIG. 1 shows the inhibition of CYP11B1 and CYP11B2 by a compound of the invention;

FIG. 2 A-D show the effect of a compound of the invention in a renal injury model;

FIG. 3 shows the effect of a compound of the invention on blood pressure in the 5/6 nephrectomy model;

FIG. 4 A-D show the effect of a compound of the invention on renal injury in the 5/6 nephrectomy model;

FIG. 5 shows the effect of a compound of the invention on renal histology in the 5/6 nephrectomy model;

FIG. 6 A-B show the effect of a compound on kidney weight as percent of body weight (A) and as a percent of pre-treatment kidney weight as a percent of body weight (B) in a genetic model of polycystic kidney disease (PCK);

FIG. 7 A-B show the effect of a compound on kidney cystic area as a percent of section area (A) and as a percent of pre-treatment cystic area as a percent of section area (B) in a genetic model of polycystic kidney disease;

DETAILED DESCRIPTION OF CERTAIN PREFERRED EMBODIMENTS OF THE INVENTION

Figure 1:
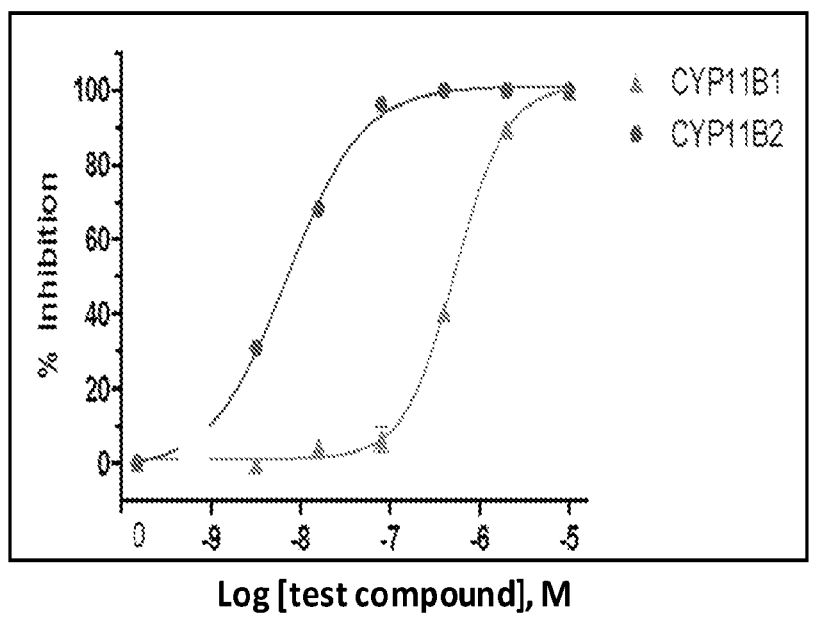

In one embodiment, certain novel inventive compounds have the structure shown in Formula (I) below:

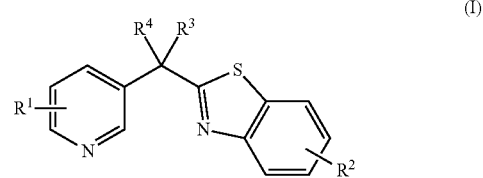

(I)

or a salt, solvate, enantiomer, ester, or hydrate thereof;
wherein $R^1$ and $R^2$ are each independently one or more H, halogen, haloalkyl, $NO_2$, CN, $COOR^5$, $SO_2R^5$, $CONR^5R^6$, $SO_2NR^5R^6$, $NR^5R^6$, $OR^5$, alkyl, alkenyl, alkynyl, heteroalkyl, aryl or hetero aryl, any of which is further substituted by one or more $R^7$; or two $R^2$ substituents taken together with the respective carbon atoms to which they are attached, form a 5-6 membered heterocyclic ring, wherein said ring is optionally substituted with one or more $R^7$;
$R^3$ is H, alkyl, alkenyl or alkynyl, any of which is further substituted by one or more $R^7$;
$R^4$ is H, $NR^5R^6$, $SR^5$, or $OR^5$;
$R^5$ and $R^6$ are independently hydrogen, alkyl, aryl, heteroaryl or haloalkyl;
$R^7$ is H, halogen, alkyl, haloalkyl, $NO_2$, CN, $COOR^8$, $SO_2R^8$, $CONR^8R^9$, $SO_2NR^8R^9$, $NR^8R^9$, or $OR^8$; and $R^8$ and $R^9$ are independently hydrogen, alkyl or haloalkyl.

In certain embodiments, each $R^1$ is independently hydrogen, fluoro, chloro, bromo, phenyl, pyridyl, isopropyl, methoxy, ethyoxy, 1-propyloxy or 2-propyloxy.

In certain embodiments, $R^1$ is 1-propyloxy or 2-propyloxy.

In certain embodiments, $R^1$ is hydrogen.
In certain embodiments, $R^1$ is fluoro.
In certain embodiments, $R^1$ is chloro.
In certain embodiments, $R^1$ is bromo.
In certain embodiments, $R^1$ is phenyl.
In certain embodiments, $R^1$ is pyridyl.
In certain embodiments, $R^1$ is isopropyl.
In certain embodiments, $R^1$ is methoxy.
In certain embodiments, $R^1$ is ethyoxy.
In certain embodiments, $R^1$ is 2-propyloxy.
In certain embodiments, $R^1$ is 1-propyloxy.

In certain embodiments, each $R^2$ is independently hydrogen, fluoro, chloro, bromo, cyano, $CONH_2$, nitro, trifluoromethyl, diisopropylamino, trifluoromethoxy, trifluoroethoxy, methoxy or phenoxy.

In certain embodiments, $R^2$ is trifluoromethyl, trifluoromethoxy or trifluoroethoxy.

In certain embodiments, $R^2$ is hydrogen.
In certain embodiments, $R^2$ is fluoro.
In certain embodiments, $R^2$ is chloro.
In certain embodiments, $R^2$ is bromo.
In certain embodiments, $R^2$ is cyano.
In certain embodiments, $R^2$ is $CONH_2$.
In certain embodiments, $R^2$ is nitro.
In certain embodiments, $R^2$ is trifluoromethyl.
In certain embodiments, $R^2$ is diisopropylamino.
In certain embodiments, $R^2$ is trifluoromethoxy.
In certain embodiments, $R^2$ is methoxy.
In certain embodiments, $R^2$ is phenoxy.
In certain embodiments $R^2$ is (4-fluoro)phenoxy.
In certain embodiments $R^2$ is (4-trifluoromethoxy)phenoxy.

In certain embodiments, two $R^2$ substituents taken together with the respective carbon atoms to which they are attached, form a 5-6 membered heterocyclic ring, wherein said ring is optionally substituted with one or more $R^7$.

In one embodiment, two $R^2$ substituents taken together with the respective carbon atoms to which they are attached is methylenedioxy, optionally further substituted with difluoro.

In certain embodiments, $R^2$ represents di-substitution with two same substituents such as difluoro, dichloro, dibromo, dimethyl, dimethoxy, ditrifluoromethyl, ditrifluoroethoxy and ditrifluoromethoxy.

In certain embodiments, $R^2$ is difluoro.
In certain embodiments, $R^2$ is dichloro.
In certain embodiments, $R^2$ is dibromo.
In certain embodiments, $R^2$ is dimethyl.
In certain embodiments, $R^2$ is dimethoxy.
In certain embodiments, $R^2$ is ditrifluoromethyl.
In certain embodiments, $R^2$ is ditrifluoromethoxy.
In certain embodiments, $R^2$ is ditrifluoroethoxy.

In certain embodiments, $R^2$ represents di-substitution with two different substituents such as fluoro and chloro, fluoro and bromo, fluoro and methoxy, chloro and methoxy, bromo and methoxy, methyl and methoxy, trifluoromethyl and methoxy, trifluoromethoxy and methoxy, fluoro and trifluoromethyl, chloro and trifluoromethyl, bromo and trifluoromethyl, methyl and trifluoromethyl, trifluoromethoxy and trifluoromethyl, fluoro and trifluoromethoxy, chloro and trifluoromethoxy, bromo and trifluoromethoxy, methyl and trifluoromethoxy, trifluoromethyl and trifluoromethoxy, fluoro and trifluoroethoxy, chloro and trifluoroethoxy, bromo and trifluoroethoxy, methyl and trifluoroethoxy, trifluoromethoxy and trifluoroethoxy or trifluoromethyl and trifluoroethoxy.

In certain embodiments, $R^2$ are fluoro and chloro.
In certain embodiments, $R^2$ are fluoro and bromo.
In certain embodiments, $R^2$ are fluoro and methoxy.
In certain embodiments, $R^2$ are chloro and methoxy.
In certain embodiments, $R^2$ are bromo and methoxy.
In certain embodiments, $R^2$ are methyl and methoxy.
In certain embodiments, $R^2$ are trifluoromethyl and methoxy.
In certain embodiments, $R^2$ are trifluoromethyl and methoxy.
In certain embodiments, $R^2$ are fluoro and trifluoromethyl.
In certain embodiments, $R^2$ are chloro and trifluoromethyl.
In certain embodiments, $R^2$ are bromo and trifluoromethyl.
In certain embodiments, $R^2$ are methyl and trifluoromethyl.
In certain embodiments, $R^2$ are trifluoromethoxy and trifluoromethyl.
In certain embodiments, $R^2$ are fluoro and trifluoromethoxy.
In certain embodiments, $R^2$ are chloro and trifluoromethoxy.
In certain embodiments, $R^2$ are bromo and trifluoromethoxy.
In certain embodiments, $R^2$ are methyl and trifluoromethoxy.
In certain embodiments, $R^2$ are trifluoromethyl and trifluoromethoxy.
In certain embodiments, $R^2$ are fluoro and trifluoroethoxy.
In certain embodiments, $R^2$ are chloro and trifluoroethoxy.
In certain embodiments, $R^2$ are bromo and trifluoroethoxy.
In certain embodiments, $R^2$ are methyl and trifluoroethoxy.
In certain embodiments, $R^2$ are trifluoromethoxy and trifluoroethoxy.
In certain embodiments, $R^2$ are trifluoromethyl and trifluoroethoxy.

In certain embodiments, $R^2$ represents tri-substitution with three same substituents such as trifluoro, trichloro or tribromo.

In certain embodiments, $R^2$ is trifluoro.
In certain embodiments, $R^2$ is trichloro.
In certain embodiments, $R^2$ is tribromo.

In certain embodiments, $R^2$ represents tri-substitution with different substituents such as difluoro and chloro, difluoro and bromo, difluoro and trifluoromethyl, difluoro and trifluoromethoxy, difluoro and trifluoroethoxy, dichloro and fluoro, dichloro and bromo, dichloro and trifluoromethyl, dichloro and trifluoromethoxy, dichloro and trifluoroethoxy, dibromo and fluoro, dibromo and chloro, dibromo and trifluoromethyl, dibromo and trifluoromethoxy, and dibromo and trifluoroethoxy.

In certain embodiments, $R^2$ are difluoro and chloro.
In certain embodiments, $R^2$ are difluoro and bromo.
In certain embodiments, $R^2$ are difluoro and trifluoromethyl.
In certain embodiments, $R^2$ are difluoro and trifluoromethoxy.

In certain embodiments, $R^2$ are difluoro and trifluoroethoxy.

In certain embodiments, $R^2$ are dichloro and fluoro.

In certain embodiments, $R^2$ are dichloro and bromo.

In certain embodiments, $R^2$ are dichloro and trifluoromethyl.

In certain embodiments, $R^2$ are dichloro and trifluoromethoxy.

In certain embodiments, $R^2$ are dichloro and trifluoroethoxy.

In certain embodiments, $R^2$ are dibromo and fluoro.

In certain embodiments, $R^2$ are dibromo and chloro.

In certain embodiments, $R^2$ are dibromo and trifluoromethyl.

In certain embodiments, $R^2$ are dibromo and trifluoromethoxy.

In certain embodiments, $R^2$ are dibromo and trifluoroethoxy.

In certain embodiments, $R^2$ are chloro, bromo and trifluoromethyl.

In certain embodiments, $R^2$ are chloro, bromo and trifluoromethoxy.

In certain embodiments, $R^3$ is hydrogen, methyl, ethyl, 1-propyl, 2-propyl, cyclopropyl, isobutyl or t-butyl.

In certain embodiments, $R^3$ is hydrogen.

In certain embodiments, $R^3$ is methyl.

In certain embodiments, $R^3$ is ethyl.

In certain embodiments, $R^3$ is 1-propyl.

In certain embodiments, $R^3$ is 2-propyl.

In certain embodiments, $R^3$ is cyclopropyl.

In certain embodiments, $R^3$ is isobutyl.

In certain embodiments, $R^3$ is t-butyl.

In certain embodiments, $R^4$ is hydrogen, SH, $NH_2$ or OH.

In certain embodiments, $R^4$ is hydrogen.

In certain embodiments, $R^4$ is SH.

In certain embodiments, $R^4$ is $NH_2$.

In certain embodiments, $R^4$ is OH.

In certain embodiments, enantiomers of the aforementioned compounds are provided, such that, for example, the definitions of substituents $R^3$ and $R^4$ are reversed.

In Formula (I), "one or more" means 1, 2, 3, or 4 independent substituents. As noted herein, when two or more $R^1$ or $R^2$ substituents are present that are not hydrogen, they may be the same or different, or a combination of two or more that are the same and one or more that is different.

The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be mixture of stereoisomers.

Moreover, some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

It will be appreciated that for each of the embodiments described above and herein, any one or more occurrences of aliphatic and/or heteroaliphatic may independently be substituted or unsubstituted, linear or branched, saturated or unsaturated; any one or more occurrences of alicyclic and/or heteroalicyclic may independently be substituted or unsubstituted, saturated or unsaturated; and any one or more occurrences of aryl and/or heteroaryl may independently be substituted or unsubstituted.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of Formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric and geometrical isomeric forms, their stereoisomers, their positional isomer, their polymorphs, their pharmaceutically acceptable salts their pharmaceutically acceptable solvates and pharmaceutically acceptable compositions containing them. Tautomeric forms of compounds of the present invention include, pyrazoles, pyridones and enols, etc., and geometrical isomers include E/Z isomers of compounds having double bonds and cis-trans isomers of monocyclic or fused ring systems, etc.

Nonlimiting examples of compounds of Formula (I) include 1-(7-bromobenzo[d]thiazol-2-yl)-1-(4-ethoxypyridin-3-yl)-2-methylpropan-1-ol; 1-(6-bromobenzo[d]thiazol-2-yl)-1-(pyridin-3-yl)butan-1-ol; 1-(6-bromobenzo[d]thiazol-2-yl)-2,2-dimethyl-1-(pyridin-3-yl)propan-1-ol; (6-bromobenzo[d]thiazol-2-yl)(cyclopropyl)(pyridin-3-yl)methanol; 1-(6-bromobenzo[d]thiazol-2-yl)-3-methyl-1-(pyridin-3-yl)butan-1-ol; 1-(benzo[d]thiazol-2-yl)-1-(pyridin-3-yl)butan-1-ol; 1-(5-bromobenzo[d]thiazol-2-yl)-2-methyl-1-(pyridin-3-yl)propan-1-ol; 1-(7-bromobenzo[d]thiazol-2-yl)-2-methyl-1-(pyridin-3-yl)propan-1-ol; 1-(6-bromobenzo[d]thiazol-2-yl)-2-methyl-1-(pyridin-3-yl)propan-1-ol; 1-(6-bromobenzo[d]thiazol-2-yl)-1-(pyridin-3-yl)propan-1-ol; 1-(6-bromobenzo[d]thiazol-2-yl)-2-methyl-1-(pyridin-3-yl)propan-1-ol; 1-(6-bromobenzo[d]thiazol-2-yl)-1-(pyridin-3-yl)ethanol; 1-(6-bromobenzo[d]thiazol-2-yl)-1-(5-methoxypyridin-3-yl)butan-1-ol; 1-(6-bromobenzo[d]thiazol-2-yl)-1-(5-chloropyridin-3-yl)butan-1-ol; 1-(6-bromobenzo[d]thiazol-2-yl)-1-(5-bromopyridin-3-yl)butan-1-ol; 1-(6-bromobenzo[d]thiazol-2-yl)-1-(5-phenylpyridin-3-yl)butan-1-ol; 1-(5-bromobenzo[d]thiazol-2-yl)-1-(5-methoxypyridin-3-yl)butan-1-ol; 1-(5-(diisopropylamino)benzo[d]thiazol-2-yl)-1-(5-methoxypyridin-3-yl)butan-1-ol;

1-(7-bromobenzo[d]thiazol-2-yl)-1-(5-methoxypyridin-3-yl)butan-1-ol; 1-(6-fluorobenzo[d]thiazol-2-yl)-1-(5-methoxypyridin-3-yl)butan-1-ol; 1-([3,3'-bipyridin]-5-yl)-1-(6-bromobenzo[d]thiazol-2-yl)butan-1-ol; 1-(7-bromobenzo[d]thiazol-2-yl)-1-(pyridin-3-yl)butan-1-ol; 1-(6-bromobenzo[d]thiazol-2-yl)-1-(6-methoxypyridin-3-yl)butan-1-ol; 1-(7-bromobenzo[d]thiazol-2-yl)-1-(4-methoxypyridin-3-yl)butan-1-ol; 1-(6-bromobenzo[d]thiazol-2-yl)-1-(4-methoxypyridin-3-yl)-2-methylpropan-1-ol; (6-bromobenzo[d]thiazol-2-yl)(4-methoxypyridin-3-yl)methanol; (7-bromobenzo[d]thiazol-2-yl)(4-methoxypyridin-3-yl)methanol; 1-(4-methoxypyridin-3-yl)-1-(6-nitrobenzo[d]thiazol-2-yl)butan-1-ol; 1-(6-bromobenzo[d]thiazol-2-yl)-1-(4-ethoxypyridin-3-yl)butan-1-ol; 1-(7-bromobenzo[d]thiazol-2-yl)-1-(4-ethoxypyridin-3-yl)butan-1-ol; 1-(benzo[d]thiazol-2-yl)-1-(4-methoxypyridin-3-yl)-2,2-dimethylpropan-1-ol; 1-(6-bromobenzo[d]thiazol-2-yl)-1-(4-ethoxypyridin-3-yl)-2-methylpropan-1-ol; 1-(6-bromobenzo[d]thiazol-2-yl)-1-(4-isopropylpyridin-3-yl)-2-methylpropan-1-ol; 1-(7-bromobenzo[d]thiazol-2-yl)-1-(4-isopropylpyridin-3-yl)-2-methylpropan-1-ol; 1-(6-bromobenzo[d]thiazol-2-yl)-1-(4-isopropoxypyridin-3-yl)-2-methylpropan-1-ol; 1-(7-bromobenzo[d]thiazol-2-yl)-1-(4-isopropoxypyridin-3-yl)-2-methylpropan-1-ol; 1-(6-bromobenzo[d]thiazol-2-yl)-1-(4-isopropylpyridin-3-yl)butan-1-ol; 1-(7-bromobenzo[d]thiazol-2-yl)-1-(4-isopropylpyridin-3-yl)butan-1-ol; 1-(6-chlorobenzo[d]thiazol-2-yl)-1-(4-ethoxypyridin-3-yl)butan-1-ol; 1-(4-ethoxypyridin-3-yl)-1-(6-nitrobenzo[d]thiazol-2-yl)butan-1-ol; 1-(4-ethoxypyridin-3-yl)-1-(6-fluorobenzo[d]thiazol-2-yl)butan-1-ol; 1-(7-chlorobenzo[d]thiazol-2-yl)-1-(4-ethoxypyridin-3-yl)butan-1-ol; 1-(4,7-difluorobenzo[d]thiazol-2-yl)-1-(4-ethoxypyridin-3-yl)butan-1-ol; 1-(4-ethoxypyridin-3-yl)-1-(7-methoxybenzo[d]thiazol-2-yl)butan-1-ol; 1-(4-ethoxypyridin-3-yl)-1-(6-(trifluoromethyl)benzo[d]thiazol-2-yl)butan-1-ol; 1-(4-ethoxypyridin-3-yl)-1-(6-(trifluoromethoxy)benzo[d]thiazol-2-yl)butan-1-ol; 1-(4-ethoxypyridin-3-yl)-1-(7-(trifluoromethyl)benzo[d]thiazol-2-yl)butan-1-ol; 1-(4-ethoxypyridin-3-yl)-1-(6-methoxybenzo[d]thiazol-2-yl)butan-1-ol; 1-(4-isopropoxypyridin-3-yl)-1-(6-(trifluoromethoxy)benzo[d]thiazol-2-yl)butan-1-ol; 1-(5,6-dichlorobenzo[d]thiazol-2-yl)-1-(4-ethoxypyridin-3-yl)butan-1-ol; 1-(4-propoxypyridin-3-yl)-1-(6-(trifluoromethoxy)benzo[d]thiazol-2-yl)butan-1-ol; 1-(2,2-difluoro-[1,3]dioxolo[4',5':4,5]benzo[1,2-d]thiazol-6-yl)-1-(4-ethoxypyridin-3-yl)butan-1-ol; 1-(7-bromobenzo[d]thiazol-2-yl)-1-(4-methoxypyridin-3-yl)-2-methylpropan-1-ol; 1-(4-ethoxypyridin-3-yl)-1-(6-(4-(trifluoromethoxy)phenoxy)benzo[d]thiazol-2-yl)butan-1-ol; 1-(4-ethoxypyridin-3-yl)-1-(6-(4-fluorophenoxy)benzo[d]thiazol-2-yl)butan-1-ol; 1-(5-bromo-6-(trifluoromethoxy)benzo[d]thiazol-2-yl)-1-(4-ethoxypyridin-3-yl)butan-1-ol; 1-(7-bromo-6-(trifluoromethoxy)benzo[d]thiazol-2-yl)-1-(4-ethoxypyridin-3-yl)butan-1-ol; 1-(5-chloro-6-(trifluoromethoxy)benzo[d]thiazol-2-yl)-1-(4-ethoxypyridin-3-yl)butan-1-ol; 1-(7-chloro-6-(trifluoromethoxy)benzo[d]thiazol-2-yl)-1-(4-ethoxypyridin-3-yl)butan-1-ol; 1-(4-ethoxypyridin-3-yl)-1-(5-methyl-6-(trifluoromethoxy)benzo[d]thiazol-2-yl)butan-1-ol; 1-(4-ethoxypyridin-3-yl)-1-(7-methyl-6-(trifluoromethoxy)benzo[d]thiazol-2-yl)butan-1-ol; (R)-1-(4-ethoxypyridin-3-yl)-1-(6-(trifluoromethoxy)-7-(trifluoromethyl)benzo[d]thiazol-2-yl)butan-1-ol; (R)-1-(6-bromobenzo[d]thiazol-2-yl)-1-(4-propoxypyridin-3-yl)butan-1-ol; (S)-1-(4-ethoxypyridin-3-yl)-1-(6-(trifluoromethoxy)-7-(trifluoromethyl)benzo[d]thiazol-2-yl)butan-1-ol; (S)-1-(6-bromobenzo[d]thiazol-2-yl)-1-(4-propoxypyridin-3-yl)butan-1-ol; 1-(4-ethoxypyridin-3-yl)-1-(6-(trifluoromethoxy)-5-(trifluoromethyl)benzo[d]thiazol-2-yl)butan-1-ol; 1-(4-ethoxypyridin-3-yl)-1-(7-methoxy-6-(trifluoromethoxy)benzo[d]thiazol-2-yl)butan-1-ol; 1-(4-propoxypyridin-3-yl)-1-(6-(trifluoromethoxy)-5-(trifluoromethyl)benzo[d]thiazol-2-yl)butan-1-ol; 1-4 propoxypyridin-3-yl)-1-(6-(trifluoromethyl)benzo[d]thiazol-2-yl)butan-1-ol; 1-(5,6-bis(trifluoromethoxy)benzo[d]thiazol-2-yl)-1-(4-ethoxypyridin-3-yl)butan-1-ol; 1-(5-bromo-6-(trifluoromethoxy)benzo[d]thiazol-2-yl)-1-(4-propoxypyridin-3-yl)butan-1-ol; 1-(6,7-bis(trifluoromethoxy)benzo[d]thiazol-2-yl)-1-(4-ethoxypyridin-3-yl)butan-1-ol; 1-(6-bromobenzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-propoxypyridin-3-yl)butan-1-ol; 1-(7-bromobenzo[d]thiazol-2-yl)-1-(4-ethoxy-5-methoxypyridin-3-yl)butan-1-ol; 1-(4-ethoxypyridin-3-yl)-1-(5-fluoro-6-(trifluoromethoxy)benzo[d]thiazol-2-yl)butan-1-ol; 1-(5-chloro-6-(trifluoromethoxy)benzo[d]thiazol-2-yl)-1-(4-propoxypyridin-3-yl)butan-1-ol; 1-(7-chloro-6-(trifluoromethoxy)benzo[d]thiazol-2-yl)-1-(4-propoxypyridin-3-yl)butan-1-ol; 1-(6-bromo-5,7-dichlorobenzo[d]thiazol-2-yl)-1-(4-propoxypyridin-3-yl)butan-1-ol; 1-(4-propoxypyridin-3-yl)-1-(5,6,7-trichlorobenzo[d]thiazol-2-yl)butan-1-ol; 1-(5,7-dichloro-6-(2,2,2-trifluoroethoxy)benzo[d]thiazol-2-yl)-1-(4-propoxypyridin-3-yl)butan-1-ol; 1-(7-chloro-6-(2,2,2-trifluoroethoxy)benzo[d]thiazol-2-yl)-1-(4-propoxypyridin-3-yl)butan-1-ol; 1-(5-chloro-6-(2,2,2-trifluoroethoxy)benzo[d]thiazol-2-yl)-1-(4-ethoxypyridin-3-yl)butan-1-ol; 1-(5,7-difluoro-6-(trifluoromethoxy)benzo[d]thiazol-2-yl)-1-(4-ethoxypyridin-3-yl)butan-1-ol; 1-(5,7-dichloro-6-(trifluoromethoxy)benzo[d]thiazol-2-yl)-1-(4-ethoxypyridin-3-yl)butan-1-ol; 1-(6-bromobenzo[d]thiazol-2-yl)-1-(4-methoxypyridin-3-yl)butan-1-ol; 1-(7-bromobenzo[d]thiazol-2-yl)-1-(4-methoxypyridin-3-yl)-2-methylpropan-1-ol; 1-(6-cyanobenzo[d]thiazol-2-yl)-1-(4-ethoxypyridin-3-yl)butan-1-ol; 2-(1-(4-ethoxypyridin-3-yl)-1-hydroxybutyl)benzo[d]thiazole-6-carboxamide; and 1-(7-bromobenzo[d]thiazol-2-yl)-1-(4-propoxypyridin-3-yl)butan-1-ol.

2) Pharmaceutical Compositions

As discussed above this invention provides novel compounds that have biological properties useful for the treatment of any of a number of conditions or diseases in which an aldosterone level lowering agent has a therapeutically useful role, or reduction in fibrosis is therapeutically beneficial.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to fibrosis. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where $R^1$ is methyl. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of other examples, carbamate and amide prodrugs of compounds of formulae (I)-(IV) are embodied herein, such as those discussed in Rautio et al., 2008, Nature Rev Drug Discov 7:255-70; Jordan et al., 2003, Bioorg Med Chem 10:2625-33 and Hay et al., 2003, J Med Chem 46:5533-45, by way of non-limiting examples.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other embodiments solid dosage forms are provided. In certain embodiments, such solid dosage forms provide a higher than about a 20% oral bioavailability. As will be shown in the examples below, compounds of the invention can be co-precipitated with one or more agents such as mannitol, a combination of mannitol and lactobionic acid, a combination of mannitol and gluconic acid, a combination of mannitol and methanesulfonic acid, a combination of microcrystalline cellulose and oleic acid or a combination of pregelatinized starch and oleic acid. The foregoing examples of one or more agents to aid in preparing formulations of inventive compound are merely illustrative and non-limiting. Non-limiting examples of inventive compounds in such solid dosage forms include The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

3) Research Uses, Clinical Uses, Pharmaceutical Uses and Methods of Treatment

Renal Disease. Chronic renal dysfunction is a progressive, degenerative disorder that ultimately results in acute renal failure and requires dialysis as an intervention, and renal transplantation as the only potential cure. Initiating conditions of renal dysfunction include ischemia, diabetes, underlying cardiovascular disease, or renal toxicity associated with certain chemotherapeutics, antibiotics, and radiocontrast agents. Most end-stage pathological changes include extensive fibrinogenesis, epithelial atrophy, and inflammatory cell infiltration into the kidneys.

Acute renal failure is often a complication of diseases including diabetes or renal ischemia, procedures such as heminephrectomy, or as a side effect of therapeutics administered to treat disease. The widely prescribed anti-tumor drug cis-diamminedichloroplatinum (cisplatin), for example, has side effects that include a high incidence of nephrotoxicity and renal dysfunction, mainly in the form of renal tubular damage that leads to impaired glomerular filtration. Administration of gentamicin, an aminoglycoside antibiotic, or cyclosporin A, a potent immunosuppressive compound, causes similar nephrotoxicity. The serious side effects of these effective drugs restrict their use. The development of agents that protect renal function and enhance renal regeneration after administration of nephrotoxic drugs will be of substantial benefit to numerous patients, especially those with malignant tumors, and may allow the maximal therapeutic potentials of these drugs to be realized. The compounds of the invention are beneficial for the treatment of the renal diseases mentioned above.

Fibrotic Liver Disease: Liver fibrosis is the scarring response of the liver to chronic liver injury; when fibrosis progresses to cirrhosis, morbid complications can develop. In fact, end-stage liver fibrosis or cirrhosis is the seventh leading cause of death in the United States, and afflicts hundreds of millions of people worldwide; deaths from end-stage liver disease in the United States are expected to triple over the next 10-15 years, mainly due to the hepatitis C epidemic. In addition to the hepatitis C virus, many other forms of chronic liver injury also lead to end-stage liver disease and cirrhosis, including other viruses such as hepatitis B and delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency).

Treatment of liver fibrosis has focused to date on eliminating the primary injury. For extrahepatic obstructions, biliary decompression is the recommended mode of treatment whereas patients with Wilson's disease are treated with zinc acetate. In chronic hepatitis C infection, interferon has been used as antiviral therapies with limited response: ~20% when used alone or ~50% response when used in combination with ribavirin. In addition to the low-level of response, treatment with interferon with or without ribavirin is associated with numerous severe side effects including neutropenia, thrombocytopenia, anemia, depression, generalized fatigue and flu-like symptoms, which are sufficiently significant to necessitate cessation of therapy. Treatments for other chronic liver diseases such as hepatitis B, autoimmune hepatitis and Wilson's disease are also associated with many side effects, while primary biliary cirrhosis, primary sclerosing cholangitis and non-alcoholic fatty liver disease have no effective treatment other than liver transplantation.

The advantage of treating fibrosis rather than only the underlying etiology, is that antifibrotic therapies should be broadly applicable across the full spectrum of chronic liver diseases. While transplantation is currently the most effective cure for liver fibrosis, mounting evidence indicates that not only fibrosis, but even cirrhosis is reversible. Unfortunately patients often present with advanced stages of fibrosis and cirrhosis, when many therapies such as antivirals can no longer be safely used due to their side effect profile. Such patients would benefit enormously from effective antifibrotic therapy, because attenuating or reversing fibrosis may prevent many late stage complications such as infection, ascites, and loss of liver function and preclude the need for liver transplantation. The compounds of the invention are beneficial for the treatment of the foregoing conditions, and generally are antifibrotic agents for this and other organ or tissues.

Hepatic Ischemia-Reperfusion Injury: Currently, transplantation is the most effective therapeutic strategy for liver fibrosis. However, in spite of the significant improvement in clinical outcome during the last decade, liver dysfunction or failure is still a significant clinical problem after transplantation surgery. Ischemia-reperfusion (IR) injury to the liver is a major alloantigen-independent component affecting transplantation outcome, causing up to 10% of early organ failure, and leading to the higher incidence of both acute and chronic rejection. Furthermore, given the dramatic organ shortage for transplantation, surgeons are forced to consider cadaveric or steatotic grafts or other marginal livers, which have a higher susceptibility to reperfusion injury. In addition to transplantation surgery, liver IR injury is manifested in clinical situations such as tissue resections (Pringle maneuver), and hemorrhagic shock.

The damage to the postischemic liver represents a continuum of processes that culminate in hepatocellular injury. Ischemia activates Kupffer cells, which are the main sources of vascular reactive oxygen species (ROS) formation during the initial reperfusion period. In addition to Kupffer cell-induced oxidant stress, with increasing length of the ischemic episode, intracellular generation of ROS by xanthine oxidase and in particular mitochondria may also contribute to liver dysfunction and cell injury during reperfusion. Endogenous antioxidant compounds, such as superoxide dismutase, catalase, glutathione, alphatocopherol, and beta-carotene, may all limit the effects of oxidant injury but these systems can quickly become overwhelmed by large quantities of ROS. Work by Lemasters and colleagues, has indicated that in addition to formation of ROS, intracellular calcium dyshomeostasis is a key contributor to liver IR injury. Cell death of hepatocytes and endothelial cells in this setting is characterized by swelling of cells and their organelles, release of cell contents, eosinophilia, karyolysis, and induction of inflammation, characteristic of oncotic necrosis. More recent reports indicate that liver cells also die by apoptosis, which is morphologically characterized by cell shrinkage, formation of apoptotic bodies with intact cell organelles and absence of an inflammatory response.

Indeed, minimizing the adverse effects of IR injury could significantly increase the number of patients that may successfully undergo liver transplantation. Pharmacologic interventions that reduce cell death and/or enhance organ regeneration represent a therapeutic approach to improve clinical outcome in liver transplantation, liver surgery with vascular exclusion and trauma and can therefore reduce recipient/patient morbidity and mortality. The compounds of the invention are beneficial for the treatment of the foregoing conditions.

Cerebral Infarction. Stroke and cerebrovascular disease are a leading cause of morbidity and mortality in the US: at least 600,000 Americans develop strokes each year, and about 160,000 of these are fatal. Research on the pathophysiological basis of stroke has produced new paradigms for prevention and treatment, but translation of these approaches into improved clinical outcomes has proved to be painfully slow. Preventive strategies focus primarily on reducing or controlling risk factors such as diabetes, hypertension, cardiovascular disease, and lifestyle; in patients with severe stenosis, carotid endarterectomy may be indicated. Cerebral angioplasty is used investigationally, but the high restenosis rates observed following coronary angioplasty suggest this approach may pose unacceptable risk for many patients. Therapeutic strategies focus primarily on acute treatment to reduce injury in the ischemic penumbra, the region of reversibly damaged tissue surrounding an infarct. Thrombolytic therapy has been shown to improve perfusion to the ischemic penumbra, but it must be administered within three hours of the onset of infarction. Several neuroprotective agents that block specific tissue responses to ischemia are promising, but none have yet been approved for clinical use. While these therapeutic approaches limit damage in the ischemic penumbra, they do not address the underlying problem of inadequate blood supply due to occluded arteries. An alternative strategy is to induce formation of collateral blood vessels in the ischemic region; this occurs naturally in chronic ischemic conditions, but stimulation of vascularization via therapeutic angiogenesis has potential therapeutic benefit.

Recent advances in imaging have confirmed the pathophysiological basis of the clinical observations of evolving stroke. Analysis of impaired cerebral blood flow (CBF) in the region of an arterial occlusion supports the hypothesis that a central region of very low CBF, the ischemic core, is irreversibly damaged, but damage in surrounding or intermixed zones where CBF is of less severely reduced, the ischemic penumbra, can be limited by timely reperfusion. The compounds of the invention are beneficial for the treatment of the foregoing conditions.

Ischemic heart disease is a leading cause of morbidity and mortality in the US, afflicting millions of Americans each year at a cost expected to exceed $300 billion/year. Numerous pharmacological and interventional approaches are being developed to improve treatment of ischemic heart disease including reduction of modifiable risk factors, improved revascularization procedures, and therapies to halt progression and/or induce regression of atherosclerosis. Atherosclerosis comprises a fibrotic component, and compounds described herein are useful for prevention and treatment as well as intervention in the development of heart failure.

Polycystic kidney disease. Autosomal recessive polycystic kidney disease (ARPKD) is a rare genetic disorder, occurring in approximately 1 in 20,000 individuals. A fibrocystic disease, patients present with progressive cystic enlargement of the kidneys and/or liver accompanied by renal and hepatic fibrosis. With no effective drug therapy for ARPKD, approximately one-third of the population presents with need for renal and/or hepatic transplantation by the age of 10 years. The compounds described here are useful for the prevention or treatment of polycystic kidney disease or autosomal recessive polycystic kidney disease.

Chronic kidney disease. As noted above, one in ten American adults have some level of chronic kidney disease (CKD), which amounts to more than 20 million US citizens. CKD occurs in both diabetic and non-diabetic nephropathies and is characterized by increasing proteinuria, declining functional nephron mass and a concomitant decline in renal function (glomerular filtration rate (GRF)<60 ml/min). It is estimated that 20-40% of diabetes patients progress to some form of CKD. In 2004, approximately 8 million people in the US were diagnosed with a glomerular filtration rate <60 ml/min. CKD often transitions to end-stage renal disease, a life-threatening condition requiring renal replacement therapy. The number of patients reaching end-stage renal disease has been increasing at an average of 7% per year over the last 10 years. Worldwide, approximately 1.1 million patients are on renal replacement therapy and this number is expected to exceed 2 million in 10 years, with 0.5 million from the US. Many people will die as a result of renal failure if renal replacement therapy is not provided. The annual mortality rate is 20% for patients on dialysis who are waiting for renal transplantation. The combined cost of dialysis and kidney transplantation is estimated to exceed $1 trillion. At present, there is no treatment reverses the course of CKD. Many patients with kidney disease benefit from antihypertensive therapy with inhibitors of angiotensin converting enzyme (ACE) or angiotensin receptor blockers (ARBs). These drugs are usually given in concert with diuretics. However, despite initial success of ACE inhibition or ARB therapy, their long term therapeutic effectiveness is often limited. There continues to be a great unmet medical need for therapies that can complement the current pharmaceutical armamentarium by slowing disease progression, reversing symptoms and delaying or preventing the need for renal replacement therapy.

The compounds of the invention are beneficial for the treatment of the chronic kidney disease as well as other forms of kidney disease.

Lung (Pulmonary) Fibrosis. Idiopathic pulmonary fibrosis (IPF) accounts for a majority of chronic interstitial lung diseases, and has an estimated incidence rate of 10.7 cases for 100,000 per year, with an estimated mortality of 50-70%. IPF is characterized by an abnormal deposition of collagen in the lung with an unknown etiology. Although the precise sequence of the pathogenic sequelae is unknown, disease progression involves epithelial injury and activation, formation of distinctive subepithelial fibroblast/myofibroblast foci, and excessive extracellular matrix accumulation. The development of this pathological process is preceded by an inflammatory response, often dominated by macrophages and lymphocytes, which is mediated by the local release of chemoattractant factors and upregulation of cell-surface adhesion molecules. Lung injury leads to vasodilatation and leakage of plasma proteins into interstitial and alveolar spaces, as well as activation of the coagulation cascade and deposition of fibrin. Fibroblasts migrate into this provisional fibrin matrix where they synthesize extracellular matrix molecules. In non-pathogenic conditions, excess fibrin is usually degraded by plasmin, a proteinase that also has a role in the activation of matrix metalloproteinases (MMPs). Activated MMPs degrade extracellular matrix and participate in fibrin removal, resulting in the clearance of the alveolar spaces and the ultimate restoration of injured tissues. In pathological conditions, however, these processes can lead to progressive and irreversible changes in lung architecture, resulting in progressive respiratory insufficiency and an almost universally terminal outcome in a relatively short period of time. Fibrosis is the final common pathway of a variety of lung disorders, and in this context, the diagnosis of pulmonary fibrosis implies the recognition of an advanced stage in the evolution of a complex process of abnormal repair. While many studies have focused on inflammatory mechanisms for initiating the fibrotic response, the synthesis and degradation the extracellular matrix represent the central event of the disease. It is this process that presents a very attractive site of therapeutic intervention.

The course of IPF is characterized by progressive respiratory insufficiency, leading to death within 3 to 8 years from the onset of symptoms. Management of interstitial lung disease in general, and in particular idiopathic pulmonary fibrosis, is difficult, unpredictable and unsatisfactory. Attempts have been made to use anti-inflammatory therapy to reverse inflammation, relief, stop disease progression and prolong survival. Corticosteroids are the most frequently used anti-inflammatory agents and have been the mainstay of therapy for IPF for more than four decades, but the efficacy of this approach is unproven, and toxicities are substantial. No studies have compared differing dosages or duration of corticosteroid treatment in matched patients. Interpretation of therapy efficacy is obscured by several factors including heterogeneous patient populations, inclusion of patients with histologic entities other than usual interstitial pneumonia, lack of objective, validated endpoints, and different criteria for "response." Cytotoxic drugs such as Azathioprine and cyclophosphamide have also being used in combination with low dose oral corticosteroids. The results of such treatments vary from no improvement to significant prolongation of survival. Overall, currently available treatments for lung fibrosis are sub-optimal. Potential new therapies have emerged from the use of animal models of pulmonary fibrosis and recent advances in the cellular and molecular biology of inflammatory reactions. Such therapies involve the use of cytokines, oxidants and growth factors that are elaborated during the fibrotic reaction. Despite the use of newer strategies for treatment, the overall prognosis for patients with interstitial lung disease has had little quantifiable change, and the population survival remains unchanged for the last 30 years. Interferon gamma (IFN) may be effective in the treatment of IPF in some patients but its role is controversial. Literature indicated that IFN-gamma may be involved in small airway disease in silicotic lung. Others showed that IFN gamma mediates, bleomycin-induced pulmonary inflammation and fibrosis. The compounds of the invention are beneficial for the treatment of the foregoing condition, among other fibrotic diseases.

Fibrosis of the skin. Scleroderma, also known as systemic sclerosis (SSc), is a connective tissue disorder characterized by abnormal thickening and formation of scar tissue in the skin (cutaneous fibrosis), lung and other organs. Scleroderma/SSc affects many body systems, but is primarily characterized by thickening and tightening of the skin. Excessive extracellular matrix (ECM) protein (principally collagen) deposition in the skin, lung and other organs is a hallmark of systemic sclerosis (SSc). Many patients who suffer from SSc also have a loss of pulmonary function. Scleroderma/SSc affects approximately 400,000 to 900,000 people in the United States every year. Mortality and morbidity in SSc are very high and are directly related to the extent of fibrosis in the involved organs. According to one study, the total cost attributed to scleroderma/SSc in the United States reached $1.5 billion annually. In this study, morbidity represented the major cost burden, associated with $820 million (55%) of the total costs. There is no known cure for scleroderma/SSc and the underlying cause remains unknown, though it is attributed to having an autoimmune component.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in a variety of such assays and models, for a number of diseases and disorders. One skilled in the art can readily determine following the guidance described herein whether a compound of the invention has antifibrotic activity.

Protection Against Renal Dysfunction. Clinical model: arterial occlusion. In a mouse model of transient unilateral renal artery occlusion, male ICR mice are anesthetized and the left renal artery occluded with a microvascular clamp. After 30 minutes, the clamp is removed and the kidney allowed to reperfuse. Ten minutes into reperfusion the nonischemic contralateral kidney is excised. Animals are treated daily with vehicle or compound of the invention (1 mg/kg, i.p.) until the day of sacrifice. Serum creatinine, BUN and urine protein levels, measured at 1, 4 and 7 days postischemia are used to determine the ability of compounds of the invention to restore function to injured kidneys. In order to create a more severe renal injury, animals are subjected to 45 minutes of ischemia.

Protection against $HgCl_2$-induced renal injury. In a study mice are injected with a high dose of $HgCl_2$ (7 mg/kg, s.c.) and divided into treatment groups. Animals in the first group receive vehicle or a compound of the invention (1 mg/kg, i.p.) on the day of toxin injection and daily thereafter for 3 days, and are euthanized on day 4. Blood samples that are collected prior to $HgCl_2$ injection, on day 2 and on day 4 are analyzed for serum creatinine. In the second group, treatment with vehicle or compound begins on the day following toxin injection (i.e., 24 h delayed treatment) and daily thereafter until day 6. Mice are euthanized on day 7. Blood samples collected prior to $HgCl_2$ injection, on day 4 and day 7 are analyzed for serum creatinine and BUN. Serum creatinine, BUN, and development of tubular necrosis are measured to indicate positive clinical activity.

Protection against ureteral obstruction. The effects of the compounds of invention on renal injury secondary to ureteral obstruction are examined in a mouse model of transient unilateral renal artery occlusion. Kidneys from mice subject to unilateral ureteral obstruction for 2 weeks are examined for histological evidence of injury and protection by compound treatment. Immunohistochemical staining is performed for fibronectin, proliferating cell nuclear antigen, and TUNEL (for an assessment of apoptosis). Trichrome staining is also performed to assess the extent of collagen formation as an indication of interstitial fibrosis.

Hepatic Disease. Antifibrotic Activity in Hepatic Stellate Cells. Serum starved (activated) LX2 cells (an immortalized human hepatic stellate cell line) that are treated with a compound of the invention show a decrease in collagen I mRNA expression, as well as expression of other fibrotic marker genes, related to significant antifibrotic activity. Liver Disease endpoints. The rat model of thioacetamide (TAA)-induced liver fibrosis and the rat bile duct ligation model of fibrosis shows improvements by the compounds of the invention, in a panel of functional and histological tests: gross morphology, mass, portal pressure, presence of ascites, enzymes (AST, ALT), collagen content, interstitial fibrosis and alpha-smooth muscle actin and MMP-2.

Cerebral infarction/stroke. Neuroprotective Effects in Brain Tissue. Cerebral infarction is induced in rats by middle cerebral artery occlusion (MCAO) for 24 hr. Test compound or vehicle is administered by i.p. at 2 mg/kg at −24, 0, and 8 hr. Sections of the brain are then examined for cell death by staining with a tetrazolium compound (2,3,5-triphenyl-2H-tetrazolium chloride, or TTC). Normal rat brains exhibit a red staining due to TTC reduction whereas areas containing dead cells are white.

Lung fibrosis. In order to assess the effects of inventive compounds on pulmonary fibrosis a well-established mouse model of bleomycin-induced lung injury is used. Male C57BL/6 mice (20-30 g, n=10/group) are treated with bleomycin (0.06 U/20 gram body weight) or saline via intratracheal administration. Bleomycin-treated mice are divided into 2 groups. Compounds of the invention or vehicle is administered daily until sacrifice on day 12 or day 20. Lung samples from the mice are then harvested for analysis. Tissues are sectioned and stained with modified Masson's Trichrome and are analyzed for interstitial fibrosis. The Ashcroft scale is used to obtain a numerical fibrotic score with each specimen being scored independently by two histopathologists, and the mean of their individual scores considered as the fibrotic score. Lung weight and hydroxyproline content are also measured as a means to assess the extent of fibrosis.

Scleroderma. A model is used in which bleomycin is subcutaneously injected into the skin is conducted in mice. Dermal hydroxyproline, dermal collagen, and dermal thickness are measures of the extent of pathology.

Pharmaceutical Uses and Methods of Treatment

As discussed above, certain of the compounds as described herein exhibit activity generally as aldosterone lowering agents. More specifically, compounds of the invention demonstrate the ability to treat diseases, conditions and symptoms resulting from increased or elevated aldosterone levels. Thus, in certain embodiments, compounds of the invention are useful for the treatment of any of a number of conditions or diseases in which inhibitors of aldosterone synthesis have a therapeutically useful role, in particular renal diseases and hypertension.

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides method for use of compounds that have biological properties useful for modulating aldosterone synthesis. In certain embodiments, the inventive compounds are useful for the treatment of chronic renal disease and hypertension. Other conditions related to elevated aldosterone levels, or hyperaldosteronism, include hypertensive vascular complications (hypertrophy followed by sclerosis of intimal smooth muscle), renal complications (sclerosis), and cardiac complications (hypertrophy followed by dilatation). Symptoms of elevated aldosterone levels treatable by the compounds, compositions and methods herein include fatigue, headache, hypokalemia, hypernatraemia, hypomagnesemia, intermittent or temporary paralysis, muscle spasms, muscle weakness, numbness, polyuria, polydipsia, tingling, and metabolic alkalosis, by way of non-limiting examples.

As discussed above this invention provides method for use of compounds that have biological properties useful for reducing fibrosis. In certain embodiments, the inventive compounds are useful for the treatment of fibrotic liver disease, hepatic ischemia-reperfusion injury, cerebral infarction, ischemic heart disease, cardiac fibrosis, renal disease or lung (pulmonary) fibrosis. In other embodiments, the disease or condition is liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; pancreatitis; renal failure; renal fibrosis; chronic kidney disease; polycystic kidney disease; scleroderma; systemic sclerosis; dermal fibrosis and idiopathic pulmonary fibrosis. In still further embodiments, the treatment is for wounds for acceleration of healing; reducing post-surgical scarring; reducing adhesion formation; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; muscular dystrophy, amyotrophic lateral sclerosis, and/or diabetes mellitus.

Thus, as described above, in another aspect of the invention, a method for the treatment of disorders related to hyperaldosteronism or elevated aldosterone levels is provided comprising administering a therapeutically effective amount of a compound of Formula (I) as described herein, to a subject in need thereof. In certain embodiments of special interest the inventive method is used for the treatment of chronic renal disease and hypertension. Other diseases of interest are described herein above. It will be appreciated that the compounds and compositions, according to the method of the present invention, may be administered using any amount and any route of administration effective for the treatment of conditions or diseases in which anti-fibrotics have a therapeutically useful role. Thus, the expression "effective amount" as used herein, refers to a sufficient amount of agent to modulate fibrosis and to exhibit a therapeutic effect. The exact amount required will vary from subject to subject, depending on the species, age, and general condition of the subject, the severity of the infection, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Compounds of the invention inhibit aldosterone synthase or CYP11B2. In certain embodiments, compounds of the invention selectively inhibit CYP11B2 compared to CYP11B1. In certain embodiments, compounds of the invention are at least two times more potent at inhibiting CYP11B2 than CYP11B1. In certain embodiments, compounds of the invention are at least five times more potent at inhibiting CYP11B2 than CYP11B1. In certain embodiments, compounds of the invention are at least ten times more potent at inhibiting CYP11B2 than CYP11B1. In certain embodiments, compounds of the invention are at least 50 times more potent at inhibiting CYP11B2 than CYP11B1. In certain embodiments, compounds of the invention are at least 100 times more potent at inhibiting CYP11B2 than CYP11B1. In certain embodiments, compounds of the invention greater than 100 times more potent at inhibiting CYP11B2 than CYP11B1.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone. Non-limiting examples of pharmaceutical agents that may be combined therapeutically with compounds of the invention include (non-limiting examples of diseases or conditions treated with such combination are indicated in parentheses): antivirals and antifibrotics, such as interferon alpha (hepatitis B, and hepatitis C), combination of interferon alpha and ribavirin (hepatitis C), Lamivudine (hepatitis B), Adefovir dipivoxil (hepatitis B), interferon gamma (idiopathic pulmonary fibrosis, liver fibrosis, and fibrosis in other organs); anticoagulants, e.g., heparin and warfarin (ischemic stroke); antiplatelets e.g., aspirin, ticlopidine and clopidogrel (ischemic stroke); other growth factors involved in regeneration, e.g., VEGF and FGF and mimetics of these growth factors; antiapoptotic agents; and motility and morphogenic agents.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures are stirred using a magnetically driven stirrer bar. An inert atmosphere refers to either dry argon or dry nitrogen. Reactions are monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures are cooled to room temperature or below then quenched, when necessary, with either water or a saturated aqueous solution of ammonium chloride. Desired products are extracted by partitioning between water and a suitable water-immiscible solvent (e.g. ethyl acetate, dichloromethane, diethyl ether). The desired product containing extracts are washed appropriately with water followed by a saturated solution of brine. On occasions where the product containing extract is deemed to contain residual oxidants, the extract is washed with a 10% solution of sodium sulphite in saturated aqueous sodium bicarbonate solution, prior to the aforementioned washing procedure. On occasions where the product containing extract is deemed to contain residual acids, the extract is washed with saturated aqueous sodium bicarbonate solution, prior to the aforementioned washing procedure (except in those cases where the desired product itself had acidic character). On occasions where the product containing extract is deemed to contain residual bases, the extract is washed with 10% aqueous citric acid solution, prior to the aforementioned washing procedure (except in those cases where the desired product itself had basic character). Post washing, the desired product containing extracts are dried over anhydrous magnesium sulphate, and then filtered. The crude products are then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes are combined and concentrated under reduced pressure at an appropriate temperature (generally less than 45° C.) to constant mass.

Example 1: 1-(7-bromobenzo[d]thiazol-2-yl)-1-(4-ethoxypyridin-3-yl)-2-methylpropan-1-ol Step-1: To a solution of 4-ethoxynicotinaldehyde (234 mg, 1.55 mmol) in THF (10 mL) at −30° C. was added isopropylmagnesium bromide (1M in THF, 1.6 mL, 1.6 mmol) and the mixture was allowed to warm to RT and stirred for 1 h. Water was added, and the mixture was evaporated under reduced pressure. To the residue was added water and extracted with dichloromethane. The organic layer was washed with brine, dried over anhydrous sodium sulfate and evaporated under reduced pressure. The crude product was purified by silica gel chromatography (ISCO CombiFlash Companion) using 0→5% methanol in DCM as eluent to afford 1-(4-ethoxypyridin-3-yl)-2-methylpropan-1-ol. 1H NMR (CDCl3, 300 MHz): δ 0.78 (d, J=6.9 Hz, 3H), 0.96 (d, J=6.9 Hz, 3H), 1.40 (t, J=7.2 Hz, 3H), 1.92-2.1 (m, 1H), 3.41 (bs, 1H), 4.05 (dq, J=6.9, 1.8 Hz, 2H), 4.55 (d, J=6.9 Hz, 1H), 6.68 (d, J=6.0 Hz, 1H), 8.27 (d, J=6.0 Hz, 1H), 8.34 (s, 1H).

Step-2: To a solution of oxalyl chloride (2M in DCM, 0.375 mL, 0.75 mmol) in dichloromethane (4 mL) at −78° C. was added drop wise dimethyl sulfoxide (0.106 mL, 1.5 mmol), and the mixture was stirred for 30 min. 1-(4-Ethoxypyridin-3-yl)-2-methylpropan-1-ol (98 mg, 0.5 mmol) in dichloromethane (2 mL) was added to the reaction mixture at −78° C. and stirring was continued for 1 h. Triethylamine (0.313 mL, 2.25 mmol) was added and the reaction was allowed to warm to RT. Water was added to the reaction mixture and was extracted with dichloromethane. The organic layer was washed with brine, dried over anhydrous sodium sulfate and evaporated under reduced pressure. The crude product was purified by silica gel chromatography (ISCO CombiFlash Companion) using 0→25% ethyl acetate in hexanes as eluent to afford 1-(4-ethoxypyridin-3-yl)-2-methylpropan-1-one. 1H NMR (CDCl3, 300 MHz): δ 1.16 (d, J=6.9 Hz, 6H), 1.49 (t, J=7.2 Hz, 3H), 3.38-3.51 (m, 1H), 4.18 (q, J=6.9 Hz, 2H), 6.83 (d, J=6.0 Hz, 1H), 8.51 (d, J=6.0 Hz, 1H), 8.63 (s, 1H).

Step-3: To a solution of 7-bromobenzo[d]thiazole (24.4 mg, 0.114 mmol) in THF (3 mL) at −78° C. was added LDA (2M in THF/hexanes, 0.068 mL, 0.137 mmol) and the mixture was stirred for 10 min. To the reaction mixture was added 1-(4-ethoxypyridin-3-yl)-2-methylpropan-1-one (22 mg, 0.114 mmol) in THF (2 mL) and the mixture was stirred at −78° C. for 30 min. The reaction was quenched with water, evaporated under reduced pressure. To the residue was added water and DCM and extracted. The DCM layer was washed with brine, dried over anhydrous sodium sulfate and evaporated under reduced pressure. Purification of the crude product by silica gel chromatography (ISCO CombiFlash Companion) using 0-5% methanol in dichloromethane as eluent afforded 1-(7-bromobenzo[d]thiazol-2-yl)-1-(4-ethoxypyridin-3-yl)-2-methylpropan-1-ol. 1H NMR (CDCl3, 300 MHz): δ 0.94 (d, J=6.9 Hz, 3H), 1.02 (d, J=6.9 Hz, 3H), 1.52 (t, J=7.2 Hz, 3H), 3.05-3.15 (m, 1H), 4.10-4.28 (m, 2H), 5.63 (s, 1H), 6.78 (d, J=3.9 Hz, 1H), 7.32 (t, J=7.8 Hz, 1H), 7.48 (dd, J=7.8, 0.3 Hz, 1H), 7.89 (dd, J=6.9, 0.9 Hz, 1H), 8.41 (d, J=5.7 Hz, 1H), 8.91 (s, 1H). MS (ES+): m/z 407.1 (M+).

Using the above procedure the following compounds have been prepared:

Example 2: 1-(6-bromobenzo[d]thiazol-2-yl)-1-(pyridin-3-yl)butan-1-ol. MS (ES+): m/z 362.01 (MH+)

Example 3: 1-(6-bromobenzo[d]thiazol-2-yl)-2,2-dimethyl-1-(pyridin-3-yl)propan-1-ol. MS (ES−): m/z 377.02 (M−1)

Example 4: (6-bromobenzo[d]thiazol-2-yl)(cyclopropyl)(pyridin-3-yl)methanol. MS (ES−): m/z 361.2 (M−1)

Example 5: 1-(6-bromobenzo[d]thiazol-2-yl)-3-methyl-1-(pyridin-3-yl)butan-1-ol. MS (ES): m/z 377.2 (M−1)

Example 6: 1-(benzo[d]thiazol-2-yl)-1-(pyridin-3-yl)butan-1-ol. MS (ES−): m/z 385.1 (M−1)

Example 7: 1-(5-bromobenzo[d]thiazol-2-yl)-2-methyl-1-(pyridin-3-yl)propan-1-ol. MS (ES+): m/z 363.27 (MH+)

Example 8: 1-(7-bromobenzo[d]thiazol-2-yl)-2-methyl-1-(pyridin-3-yl)propan-1-ol. MS (ES+): m/z 363.2 (MH+)

Example 9: 1-(6-bromobenzo[d]thiazol-2-yl)-2-methyl-1-(pyridin-3-yl)propan-1-ol. MS (ES+): m/z 362.01 (MH+)

Example 10: 1-(6-bromobenzo[d]thiazol-2-yl)-1-(pyridin-3-yl)propan-1-ol. MS (ES+): m/z 349.2 (MH+)

Example 11: 1-(6-bromobenzo[d]thiazol-2-yl)-2-methyl-1-(pyridin-3-yl)propan-1-ol. MS (ES+): m/z 363.2 (MH+)

Example 12: 1-(6-bromobenzo[d]thiazol-2-yl)-1-(pyridin-3-yl)ethanol. MS (ES+): m/z 335.2 (MH+)

Example 13: 1-(6-bromobenzo[d]thiazol-2-yl)-1-(5-methoxypyridin-3-yl)butan-1-ol. MS (ES+): m/z 393.2 (MH+)

Example 14: 1-(6-bromobenzo[d]thiazol-2-yl)-1-(5-chloropyridin-3-yl)butan-1-ol. MS (ES+): m/z 397.2 (MH+)

Example 15: 1-(6-bromobenzo[d]thiazol-2-yl)-1-(5-bromopyridin-3-yl)butan-1-ol. MS (ES+): m/z 443.2 (MH+)

Example 16: 1-(6-bromobenzo[d]thiazol-2-yl)-1-(5-phenylpyridin-3-yl)butan-1-ol. MS (ES+): m/z 439.2 (MH+)

Example 17: 1-(5-bromobenzo[d]thiazol-2-yl)-1-(5-methoxypyridin-3-yl)butan-1-ol. MS (ES+): m/z 393.2 (MH+)

Example 18: 1-(5-(diisopropylamino)benzo[d]thiazol-2-yl)-1-(5-methoxypyridin-3-yl)butan-1-ol. MS (ES+): m/z 414.2 (MH+)

Example 19: 1-(7-bromobenzo[d]thiazol-2-yl)-1-(5-methoxypyridin-3-yl)butan-1-ol. MS (ES+): m/z 393.2 (MH+)

Example 20: 1-(6-fluorobenzo[d]thiazol-2-yl)-1-(5-methoxypyridin-3-yl)butan-1-ol. MS (ES+): m/z 333.2 (MH+)

Example 21: 1-([3,3'-bipyridin]-5-yl)-1-(6-bromobenzo[d]thiazol-2-yl)butan-1-ol. MS (ES+): m/z 440.2 (MH+)

Example 22: 1-(7-bromobenzo[d]thiazol-2-yl)-1-(pyridin-3-yl)butan-1-ol. MS (ES+): m/z 363.2 (MH+)

Example 23: 1-(6-bromobenzo[d]thiazol-2-yl)-1-(6-methoxypyridin-3-yl)butan-1-ol. MS (ES+): m/z 393.1 (MH+)

Example 24: 1-(7-bromobenzo[d]thiazol-2-yl)-1-(4-methoxypyridin-3-yl)butan-1-ol. MS (ES+): m/z 393 (MH+)

Example 25: 1-(6-bromobenzo[d]thiazol-2-yl)-1-(4-methoxypyridin-3-yl)-2-methylpropan-1-ol. MS (ES+): m/z 393 (MH+)

Example 26: (6-bromobenzo[d]thiazol-2-yl)(4-methoxypyridin-3-yl)methanol. MS (ES+): m/z 351 (MH+)

Example 27: (7-bromobenzo[d]thiazol-2-yl)(4-methoxypyridin-3-yl)methanol. MS (ES+): m/z 351 (MH+)

Example 28: 1-(4-methoxypyridin-3-yl)-1-(6-nitrobenzo[d]thiazol-2-yl)butan-1-ol. MS (ES+): m/z 360.1 (MH+)

Example 29: 1-(6-bromobenzo[d]thiazol-2-yl)-1-(4-ethoxypyridin-3-yl)butan-1-ol. MS (ES+): m/z 407.1 (MH+)

Example 30: 1-(7-bromobenzo[d]thiazol-2-yl)-1-(4-ethoxypyridin-3-yl)butan-1-ol. MS (ES+): m/z 407.1 (MH+)

Example 31: 1-(benzo[d]thiazol-2-yl)-1-(4-methoxypyridin-3-yl)-2,2-dimethylpropan-1-ol. MS (ES+): m/z 329.1 (MH+)

Example 32: 1-(6-bromobenzo[d]thiazol-2-yl)-1-(4-ethoxypyridin-3-yl)-2-methylpropan-1-ol. MS (ES+): m/z 407.1 (MH+)

Example 33: 1-(6-bromobenzo[d]thiazol-2-yl)-1-(4-isopropylpyridin-3-yl)-2-methylpropan-1-ol. MS (ES+): m/z 405.1 (MH+)

Example 34: 1-(7-bromobenzo[d]thiazol-2-yl)-1-(4-isopropylpyridin-3-yl)-2-methylpropan-1-ol. MS (ES+): m/z 405.1 (MH+)

Example 35: 1-(6-bromobenzo[d]thiazol-2-yl)-1-(4-isopropoxypyridin-3-yl)-2-methylpropan-1-ol. MS (ES+): m/z 421.1 (MH+)

Example 36: 1-(7-bromobenzo[d]thiazol-2-yl)-1-(4-isopropoxypyridin-3-yl)-2-methylpropan-1-ol. MS (ES+): m/z 421.1 (MH+)

Example 37: 1-(6-bromobenzo[d]thiazol-2-yl)-1-(4-isopropylpyridin-3-yl)butan-1-ol. MS (ES+): m/z 405.1 (MH+)

Example 38: 1-(7-bromobenzo[d]thiazol-2-yl)-1-(4-isopropylpyridin-3-yl)butan-1-ol. MS (ES+): m/z 405.1 (MH+)

Example 39: 1-(6-chlorobenzo[d]thiazol-2-yl)-1-(4-ethoxypyridin-3-yl)butan-1-ol. MS (ES+): m/z 363.1 (MH+)

Example 40: 1-(4-ethoxypyridin-3-yl)-1-(6-nitrobenzo[d]thiazol-2-yl)butan-1-ol. MS (ES+): m/z 374.1 (MH+)

Example 41: 1-(4-ethoxypyridin-3-yl)-1-(6-fluorobenzo[d]thiazol-2-yl)butan-1-ol. MS (ES+): m/z 347.1 (MH+)

Example 42: 1-(7-chlorobenzo[d]thiazol-2-yl)-1-(4-ethoxypyridin-3-yl)butan-1-ol. MS (ES+): m/z 363.1 (MH+)

Example 43: 1-(4,7-difluorobenzo[d]thiazol-2-yl)-1-(4-ethoxypyridin-3-yl)butan-1-ol. MS (ES+): m/z 365.16 (MH+)

Example 44: 1-(4-ethoxypyridin-3-yl)-1-(7-methoxybenzo[d]thiazol-2-yl)butan-1-ol. MS (ES+): m/z 359.2 (MH+)

Example 45: 1-(4-ethoxypyridin-3-yl)-1-(6-(trifluoromethyl)benzo[d]thiazol-2-yl)butan-1-ol. MS (ES+): m/z 397.1 (MH+)

Example 46: 1-(4-ethoxypyridin-3-yl)-1-(6-(trifluoromethoxy)benzo[d]thiazol-2-yl)butan-1-ol. MS (ES+): m/z 413.1 (MH+)

Example 47: 1-(4-ethoxypyridin-3-yl)-1-(7-(trifluoromethyl)benzo[d]thiazol-2-yl)butan-1-ol. MS (ES+): m/z 397.1 (MH+)

Example 48: 1-(4-ethoxypyridin-3-yl)-1-(6-methoxybenzo[d]thiazol-2-yl)butan-1-ol. MS (ES+): m/z 359.2 (MH+)

Example 49: 1-(4-isopropoxypyridin-3-yl)-1-(6-(trifluoromethoxy)benzo[d]thiazol-2-yl)butan-1-ol. MS (ES+): m/z 427.1 (MH+)

Example 50: 1-(5,6-dichlorobenzo[d]thiazol-2-yl)-1-(4-ethoxypyridin-3-yl)butan-1-ol. MS (ES+): m/z 397.1

Example 51: 1-(4-propoxypyridin-3-yl)-1-(6-(trifluoromethoxy)benzo[d]thiazol-2-yl)butan-1-ol. MS (ES+): m/z 427.1 (MH+)

Example 52: 1-(2,2-difluoro-[1,3]dioxolo[4',5':4,5]benzo[1,2-d]thiazol-6-yl)-1-(4-ethoxypyridin-3-yl)butan-1-ol. MS (ES+): m/z 409.1 (MH+)

Example 53: 1-(7-bromobenzo[d]thiazol-2-yl)-1-(4-methoxypyridin-3-yl)-2-methylpropan-1-ol. MS (ES+): m/z 393.1 (MH+)

Example 54: 1-(4-ethoxypyridin-3-yl)-1-(6-(4-(trifluoromethoxy)phenoxy)benzo[d]thiazol-2-yl)butan-1-ol. MS (ES+): m/z 505.14 (MH+)

Example 55: 1-(4-ethoxypyridin-3-yl)-1-(6-(4-fluorophenoxy)benzo[d]thiazol-2-yl)butan-1-ol. MS (ES+): m/z 439.12 (MH+)

Example 56: 1-(5-bromo-6-(trifluoromethoxy)benzo[d]thiazol-2-yl)-1-(4-ethoxypyridin-3-yl)butan-1-ol. MS (ES+): m/z 493.03 (MH+)

Example 57: 1-(7-bromo-6-(trifluoromethoxy)benzo[d]thiazol-2-yl)-1-(4-ethoxypyridin-3-yl)butan-1-ol. MS (ES+): m/z 491.00 (M+)

Example 58: 1-(5-chloro-6-(trifluoromethoxy)benzo[d]thiazol-2-yl)-1-(4-ethoxypyridin-3-yl)butan-1-ol. MS (ES+): m/z 447.05 (MH+)

Example 59: 1-(7-chloro-6-(trifluoromethoxy)benzo[d]thiazol-2-yl)-1-(4-ethoxypyridin-3-yl)butan-1-ol. MS (ES+): m/z 447.20 (MH+)

Example 60: 1-(4-ethoxypyridin-3-yl)-1-(5-methyl-6-(trifluoromethoxy)benzo[d]thiazol-2-yl)butan-1-ol. MS (ES+): m/z 427.10 (MH+)

Example 61: 1-(4-ethoxypyridin-3-yl)-1-(7-methyl-6-(trifluoromethoxy)benzo[d]thiazol-2-yl)butan-1-ol. MS (ES+): m/z 427.10 (MH+)

Example 62: 1-(4-ethoxypyridin-3-yl)-1-(5-fluoro-6-(trifluoromethoxy)benzo[d]thiazol-2-yl)butan-1-ol. MS (ES+): m/z 431.15 (MH+)

Example 63: 1-(5-chloro-6-(trifluoromethoxy)benzo[d]thiazol-2-yl)-1-(4-propoxypyridin-3-yl)butan-1-ol. MS (ES+): m/z 461.13 (MH+)

Example 64: 1-(7-chloro-6-(trifluoromethoxy)benzo[d]thiazol-2-yl)-1-(4-propoxypyridin-3-yl)butan-1-ol. MS (ES+): m/z 461.13 (MH+)

Example 65: 1-(6-bromo-5,7-dichlorobenzo[d]thiazol-2-yl)-1-(4-propoxypyridin-3-yl)butan-1-ol. MS (ES+): m/z 476.94 (M+)

Example 66: 1-(4-propoxypyridin-3-yl)-1-(5,6,7-trichlorobenzo[d]thiazol-2-yl)butan-1-ol. MS (ES+): m/z 430.99 (M+)

Example 67: 1-(5,7-dichloro-6-(2,2,2-trifluoroethoxy)benzo[d]thiazol-2-yl)-1-(4-propoxypyridin-3-yl)butan-1-ol. MS (ES+): m/z 495.04 (M+)

Example 68: 1-(7-chloro-6-(2,2,2-trifluoroethoxy)benzo[d]thiazol-2-yl)-1-(4-propoxypyridin-3-yl)butan-1-ol. MS (ES+): m/z 461.07 (MH+)

Example 69: 1-(5-chloro-6-(2,2,2-trifluoroethoxy)benzo[d]thiazol-2-yl)-1-(4-ethoxypyridin-3-yl)butan-1-ol. MS (ES+): m/z 461.3 (MH+)

Example 70: 1-(6-bromobenzo[d]thiazol-2-yl)-1-(4-methoxypyridin-3-yl)butan-1-ol. MS (ES+): m/z 393.2 (M+)

Example 71: 1-(7-bromobenzo[d]thiazol-2-yl)-1-(4-methoxypyridin-3-yl)-2-methylpropan-1-ol MS (ES+): m/z 393.1 (M+)

Example 72: 1-(6-cyanobenzo[d]thiazol-2-yl)-1-(4-ethoxypyridin-3-yl)butan-1-ol. MS (ES+): m/z 354.2 (MH+)

Example 73: 2-(1-(4-ethoxypyridin-3-yl)-1-hydroxybutyl)benzo[d]thiazole-6-carboxamide. MS (ES+): m/z 372.2 (MH+)

Using the above procedure, the following compounds can also be prepared: (R)-1-(4-ethoxypyridin-3-yl)-1-(6-(trifluoromethoxy)-7-(trifluoromethyl)benzo[d]thiazol-2-yl)butan-1-ol; (R)-1-(6-bromobenzo[d]thiazol-2-yl)-1-(4-propoxypyridin-3-yl)butan-1-ol; (S)-1-(4-ethoxypyridin-3-yl)-1-(6-(trifluoromethoxy)-7-(trifluoromethyl)benzo[d]thiazol-2-yl)butan-1-ol; (S)-1-(6-bromobenzo[d]thiazol-2-yl)-1-(4-propoxypyridin-3-yl)butan-1-ol; 1-(4-ethoxypyridin-3-yl)-1-(6-(trifluoromethoxy)-5-(trifluoromethyl)benzo[d]thiazol-2-yl)butan-1-ol; 1-(4-ethoxypyridin-3-yl)-1-(7-methoxy-6-(trifluoromethoxy)benzo[d]thiazol-2-yl)butan-1-ol; 1-(4-propoxypyridin-3-yl)-1-(6-(trifluoromethoxy)-5-(trifluoromethyl)benzo[d]thiazol-2-yl)butan-1-ol; 1-(4-propoxypyridin-3-yl)-1-(6-(trifluoromethyl)benzo[d]thiazol-2-yl)butan-1-1 ol; 1-(5,6-bis(trifluoromethoxy)benzo[d]thiazol-2-yl)-1-(4-ethoxypyridin-3-yl)butan-1-ol; 1-(5-bromo-6-(trifluoromethoxy)benzo[d]thiazol-2-yl)-1-(4-propoxypyridin-3-yl)butan-1-ol; 1-(6,7-bis(trifluoromethoxy)benzo[d]thiazol-2-yl)-1-(4-ethoxypyridin-3-yl)butan-1-ol; 1-(6-bromobenzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-propoxypyridin-3-yl)butan-1-ol; 1-(7-bromobenzo[d]thiazol-2-yl)-1-(4-ethoxy-5-methoxypyridin-3-yl)butan-1-ol; 1-(5,7-difluoro-6-(trifluoromethoxy)benzo[d]thiazol-2-yl)-1-(4-ethoxypyridin-3-yl)butan-1-ol; 1-(5,7-dichloro-6-(trifluoromethoxy)benzo[d]thiazol-2-yl)-1-(4-ethoxypyridin-3-yl)butan-1-ol and 1-(7-bromobenzo[d]thiazol-2-yl)-1-(4-propoxypyridin-3-yl)butan-1-ol.

Example 74: Assessment of Aldosterone Inhibitory Activity

For the determination of aldosterone inhibitory activity, tests were carried out using V79 Chinese hamster cells stably transfected with human CYP11B2 or CYP11B1 and using assay protocols as described in Ehmer P B, Bureik M, Bernhardt R, Muller U, Hartmann R W. Development of a test system for inhibitors of human aldosterone synthase (CYP11B2): screening in fission yeast and evaluation of selectivity in V79 cells. J. Steroid Biochem. Mol. Biol. 2002 June; 81(2):173-9. The concentration of the substrate 11-deoxycorticosterone in the assay was 100 nM. FIG. 1 shows for one exemplary compound that the inhibition of the product of gene CYP11B2, aldosterone synthase, is high whereas the inhibition of the related enzyme CYP11B1 is significantly less, by a factor of about 70 fold.

The following compounds of Formula (I) inhibited the production of aldosterone with an IC50 of <1 μM in V79 Chinese hamster cells. 1-(7-bromobenzo[d]thiazol-2-yl)-1-(4-ethoxypyridin-3-yl)-2-methylpropan-1-ol; 1-(6-fluorobenzo[d]thiazol-2-yl)-1-(5-methoxypyridin-3-yl)butan-1-ol; 1-(7-bromobenzo[d]thiazol-2-yl)-1-(4-methoxypyridin-3-yl)butan-1-ol; 1-(6-bromobenzo[d]thiazol-2-yl)-1-(4-methoxypyridin-3-yl)-2-methylpropan-1-ol; (6-bromobenzo[d]thiazol-2-yl)(4-methoxypyridin-3-yl)methanol; (7-bromobenzo[d]thiazol-2-yl)(4-methoxypyridin-3-yl)methanol; 1-(4-methoxypyridin-3-yl)-1-(6-nitrobenzo[d]thiazol-2-yl)butan-1-ol; 1-(6-bromobenzo[d]thiazol-2-yl)-1-(4-ethoxypyridin-3-yl)butan-1-ol; 1-(7-bromobenzo[d]thiazol-2-yl)-1-(4-ethoxypyridin-3-yl)butan-1-ol; 1-(benzo[d]thiazol-2-yl)-1-(4-methoxypyridin-3-yl)-2,2-dimethylpropan-1-ol; 1-(6-bromobenzo[d]thiazol-2-yl)-1-(4-ethoxypyridin-3-yl)-2-methylpropan-1-ol; 1-(6-bromobenzo[d]thiazol-2-yl)-1-(4-isopropylpyridin-3-yl)-2-methylpropan-1-ol; 1-(7-bromobenzo[d]thiazol-2-yl)-1-(4-isopropylpyridin-3-yl)-2-methylpropan-1-ol; 1-(6-bromobenzo[d]thiazol-2-yl)-1-(4-isopropoxypyridin-3-yl)-2-methylpropan-1-ol; 1-(7-bromobenzo[d]thiazol-2-yl)-1-(4-isopropoxypyridin-3-yl)-2-methylpropan-1-ol; 1-(6-bromobenzo[d]thiazol-2-yl)-1-(4-isopropylpyridin-3-yl)butan-1-ol; 1-(7-bromobenzo[d]thiazol-2-yl)-1-(4-isopropylpyridin-3-yl)butan-1-ol; 1-(6-chlorobenzo[d]thiazol-2-yl)-1-(4-ethoxypyridin-3-yl)butan-1-ol; 1-(4-ethoxypyridin-3-yl)-1-(6-nitrobenzo[d]thiazol-2-yl)butan-1-ol; 1-(4-ethoxypyridin-3-yl)-1-(6-fluorobenzo[d]thiazol-2-yl)butan-1-ol; 1-(7-chlorobenzo[d]thiazol-2-yl)-1-(4-ethoxypyridin-3-yl)butan-1-ol; 1-(4,7-difluorobenzo[d]thiazol-2-yl)-1-(4-ethoxypyridin-3-yl)butan-1-ol; 1-(4-ethoxypyridin-3-yl)-1-(7-methoxybenzo[d]thiazol-2-yl)butan-1-ol; 1-(4-ethoxypyridin-3-yl)-1-(6-(trifluoromethyl)benzo[d]thiazol-2-yl)butan-1-ol; 1-(4-ethoxypyridin-3-yl)-1-(6-(trifluoromethoxy)benzo[d]thiazol-2-yl)butan-1-ol; 1-(4-ethoxypyridin-3-yl)-1-(7-(trifluoromethyl)benzo[d]thiazol-2-yl)butan-1-ol; 1-(4-ethoxypyridin-3-yl)-1-(6-methoxybenzo[d]thiazol-2-yl)butan-1-ol; 1-(4-isopropoxypyridin-3-yl)-1-(6-(trifluoromethoxy)benzo[d]thiazol-2-yl)butan-1-ol; 1-(5,6-dichlorobenzo[d]thiazol-2-yl)-1-(4-ethoxypyridin-3-yl)butan-1-ol; 1-(4-propoxypyridin-3-yl)-1-(6-(trifluoromethoxy)benzo[d]thiazol-2-yl)butan-1-ol; 1-(2,2-difluoro-[1,3]dioxolo[4',5':4,5]benzo[1,2-d]thiazol-6-yl)-1-(4-ethoxypyridin-3-yl)butan-1-ol; 1-(7-bromobenzo[d]thiazol-2-yl)-1-(4-methoxypyridin-3-yl)-2-methylpropan-1-ol; 1-(4-ethoxypyridin-3-yl)-1-(6-(4-(trifluoromethoxy)phenoxy)benzo[d]thiazol-2-yl)butan-1-ol; 1-(4-ethoxypyridin-3-yl)-1-(6-(4-fluorophenoxy)benzo[d]thiazol-2-yl)butan-1-ol; 1-(5-bromo-6-(trifluoromethoxy)benzo[d]thiazol-2-yl)-1-(4-ethoxypyridin-3-yl)butan-1-ol; 1-(7-bromo-6-(trifluoromethoxy)benzo[d]thiazol-2-yl)-1-(4-ethoxypyridin-3-yl)butan-1-ol; 1-(5-chloro-6-(trifluoromethoxy)benzo[d]thiazol-2-yl)-1-(4-ethoxypyridin-3-yl)butan-1-ol; 1-(7-chloro-6-(trifluoromethoxy)benzo[d]thiazol-2-yl)-1-(4-ethoxypyridin-3-yl)butan-1-ol; 1-(4-ethoxypyridin-3-yl)-1-(5-methyl-6-(trifluoromethoxy)benzo[d]thiazol-2-yl)butan-1-ol; 1-(4-ethoxypyridin-3-yl)-1-(7-methyl-6-(trifluoromethoxy)benzo[d]thiazol-2-yl)butan-1-ol; 1-(4-ethoxypyridin-3-yl)-1-(5-fluoro-6-(trifluoromethoxy)benzo[d]thiazol-2-yl)butan-1-ol; 1-(5-chloro-6-(trifluoromethoxy)benzo[d]thiazol-2-yl)-1-(4-propoxypyridin-3-yl)butan-1-ol; 1-(7-chloro-6-(trifluoromethoxy)benzo[d]thiazol-2-yl)-1-(4-propoxypyridin-3-yl)butan-1-ol; 1-(6-bromo-5,7-dichlorobenzo[d]thiazol-2-yl)-1-(4-propoxypyridin-3-yl)butan-1-ol; 1-(4-propoxypyridin-3-yl)-1-(5,6,7-trichlorobenzo[d]thiazol-2-yl)butan-1-ol; 1-(5,7-dichloro-6-(2,2,2-trifluoroethoxy)benzo[d]thiazol-2-yl)-1-(4-propoxypyridin-3-yl)butan-1-ol; 1-(7-chloro-6-(2,2,2-trifluoroethoxy)benzo[d]thiazol-2-yl)-1-(4-propoxypyridin-3-yl)butan-1-ol; 1-(5-chloro-6-(2,2,2-trifluoroethoxy)benzo[d]thiazol-2-yl)-1-(4-ethoxypyridin-3-yl)butan-1-ol; 1-(6-bromobenzo[d]thiazol-2-yl)-1-(4-methoxypyridin-3-yl)butan-1-ol; 1-(7-bromobenzo[d]thiazol-2-yl)-1-(4-methoxypyridin-3-yl)-2-methylpropan-1-ol; 1-(6-cyanobenzo[d]thiazol-2-yl)-1-(4-ethoxypyridin-3-yl)butan-1-ol; 2-(1-(4-ethoxypyridin-3-yl)-1-hydroxybutyl)benzo[d]thiazole-6-carboxamide.

Example 75: Assessment of Aldosterone Synthase Inhibitory Activity

To test the activity of compounds in a cell-based assay, a well-established assay described in the literature was used [Muller-Vieira U, Angotti M, Hartmann R W. The adrenocortical tumor cell line NCI-H295R as an in vitro screening system for the evaluation of CYP11B2 (aldosterone synthase) and CYP11B1 (steroid-11beta-hydroxylase) inhibitors. J Steroid Biochem Mol Biol 2005 August; 96(3-4): 259-70; Ulleras E, Ohlsson A, Oskarsson A. Secretion of cortisol and aldosterone as a vulnerable target for adrenal endocrine disruption-screening of 30 selected chemicals in the human H295R cell model. J Appl Toxicol 2008 November; 28(8):1045-53; Jager L P, De Graaf G J, Widjaja-Greefkes H C. Screening for drug-induced alterations in the production and release of steroid hormones by porcine adrenocortical cells in vitro. Toxicol In Vitro 1996 October; 10(5):595-608.]. In brief, human adrenocortical carcinoma cells (H295R; ATCC CRL-2128) were plated in 96-well plates and the effect of compounds on angiotensin-II (Ang-II) stimulated aldosterone production was determined in the supernatant using an ELISA kit (Genway 40-521-475012). Positive control compounds such as etomidate and the promiscuous P450 inhibitor ketoconazole significantly inhibited both the basal and the Ang-II stimulated aldosterone production in this assay. Compounds were tested in the aldosterone production assay at various concentrations and from dose-response inhibition curves the % inhibition at specific concentrations and the IC50 were calculated.

The following compounds of Formula (I) inhibited the production of aldosterone with an $IC_{50}$ of 1 µM-10 µM in NCI-H295R cells. 1-(6-bromobenzo[d]thiazol-2-yl)-1-(pyridin-3-yl)butan-1-ol; 1-(6-bromobenzo[d]thiazol-2-yl)-2,2-dimethyl-1-(pyridin-3-yl)propan-1-ol; (6-bromobenzo[d]thiazol-2-yl)(cyclopropyl)(pyridin-3-yl)methanol; 1-(6-bromobenzo[d]thiazol-2-yl)-3-methyl-1-(pyridin-3-yl)butan-1-ol; 1-(benzo[d]thiazol-2-yl)-1-(pyridin-3-yl)butan-1-ol; 1-(5-bromobenzo[d]thiazol-2-yl)-2-methyl-1-(pyridin-3-yl)propan-1-ol; 1-(7-bromobenzo[d]thiazol-2-yl)-2-methyl-1-(pyridin-3-yl)propan-1-ol; 1-(6-bromobenzo[d]thiazol-2-yl)-2-methyl-1-(pyridin-3-yl)propan-1-ol; 1-(6-bromobenzo[d]thiazol-2-yl)-1-(pyridin-3-yl)propan-1-ol; 1-(6-bromobenzo[d]thiazol-2-yl)-1-(pyridin-3-yl)ethanol; 1-(6-bromobenzo[d]thiazol-2-yl)-1-(5-methoxypyridin-3-yl)butan-1-ol; 1-(6-bromobenzo[d]thiazol-2-yl)-1-(5-chloropyridin-3-yl)butan-1-ol; 1-(6-bromobenzo[d]thiazol-2-yl)-1-(5-bromopyridin-3-yl)butan-1-ol; 1-(6-bromobenzo[d]thiazol-2-yl)-1-(5-phenylpyridin-3-yl)butan-1-ol; 1-(7-bromobenzo[d]thiazol-2-yl)-1-(5-methoxypyridin-3-yl)butan-1-ol; 1-([3,3'-bipyridin]-5-yl)-1-(6-bromobenzo[d]thiazol-2-yl)butan-1-ol; and 1-(7-bromobenzo[d]thiazol-2-yl)-1-(pyridin-3-yl)butan-1-ol.

Example 76: Test Compound Ameliorates Renal Fibrosis in the Mouse UUO Model

An exemplary compound was tested in the mouse unilateral urethral obstruction (UUO) model. Adult male mice were subjected to UUO via ligation of the left renal artery, while keeping the contralateral right kidney intact. In this model, marked induction of fibrosis is observed as early as four days after UUO and this is seen to progress in animals sacrificed ten days after UUO.

Figure 2:
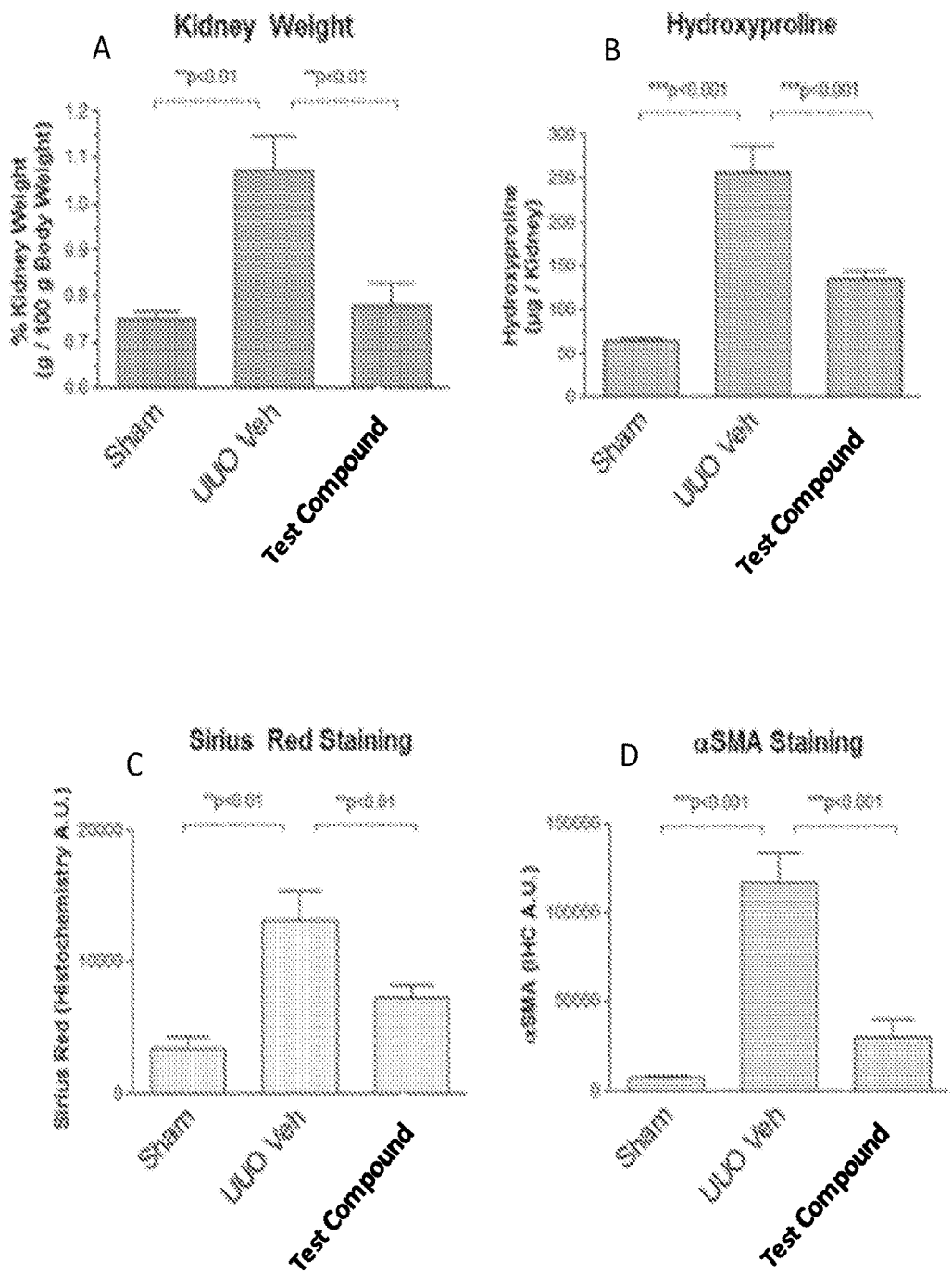

Starting the day of UUO, animals were treated orally with 25 mg/kg of compound twice every day for 10 days. Test compound reduced the increase in kidney weight (FIG. 2A) and kidney collagen deposition (hydroxyproline and Sirius Red Staining, FIGS. 2B and 2C, respectively) observed in the vehicle treated group. Test compound also affected alpha smooth muscle actin staining (FIG. 2D), which is another, early biomarker for the development of fibrosis. Overall, these observations indicate that aldosterone synthase inhibition has an anti-fibrotic activity in the mouse UUO model. Since the UUO does not result in increased blood pressure, the anti-fibrotic activity of the test compound is not likely to be due to blood pressure lowering activity.

Figure 3:
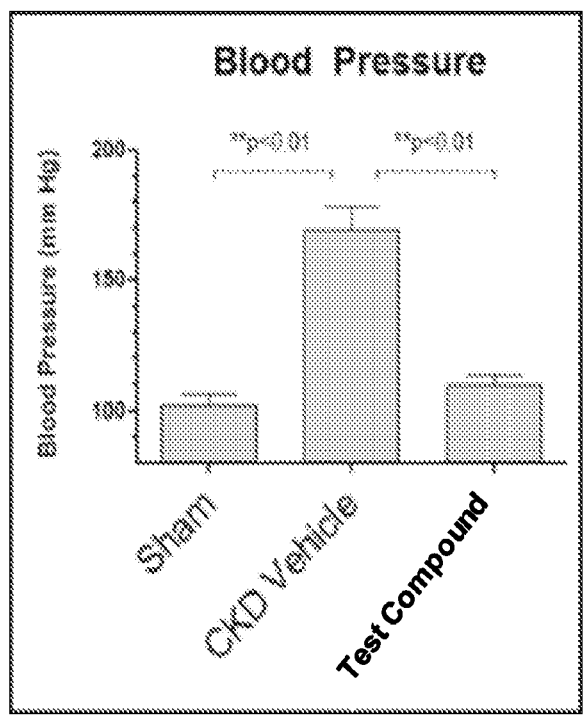

Example 77: Test Compound Improves Renal Function in the Rat Remnant Kidney Model of CKD The effect of test compound was also tested in the rat remnant kidney model. Animals were subjected to 5/6 nephrectomy and placed in metabolic cages to collect urine samples for determination of albuminuria. Marked increases were found in urine albumin levels, as well as elevated serum BUN and creatinine concentration. The rats with overt renal dysfunction were then randomized to vehicle and test compound (25 mg/kg, po, bid) treatment groups. After one month of compound or vehicle treatment, and prior to sacrifice, urine was collected for urine analysis, and blood pressure was measured to determine the effects of test compound on blood pressure. While 5/6 nephrectomy—as expected—markedly elevated the blood pressure, this elevated BP was reduced to normal by test compound treatment (FIG. 3). Test compound markedly reduced serum BUN and creatinine levels (FIG. 4A; left bar, BUN; right bar, creatinine), kidney collagen content (as determined by hydroxyproline assay; FIG. 4B) and improved renal histology (FIG. 5), both in the structural integrity of glomeruli as of proximal and distal convoluted tubules. Importantly, renal function, as determined by urine albumin to creatinine ratio (FIG. 4C) and by the concentration of neutrophil gelatinase-associated lipocalin (NGAL; a sensitive urine biomarker of tubule-interstitial injury) in the urine (FIG. 4D), showed marked improvements. Taken together, this study indicated marked improvement in renal function by compound treatment compared to animals receiving vehicle treatment.

Figure 6:
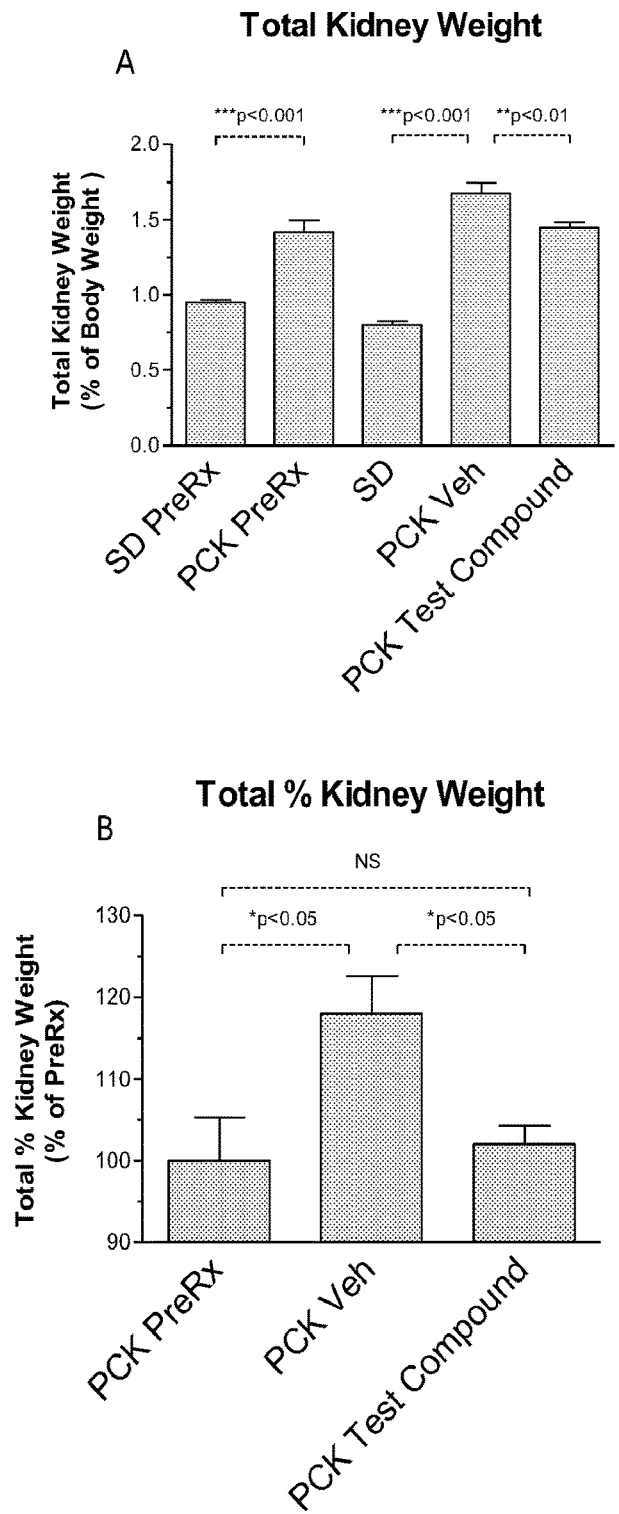
Figure 7:
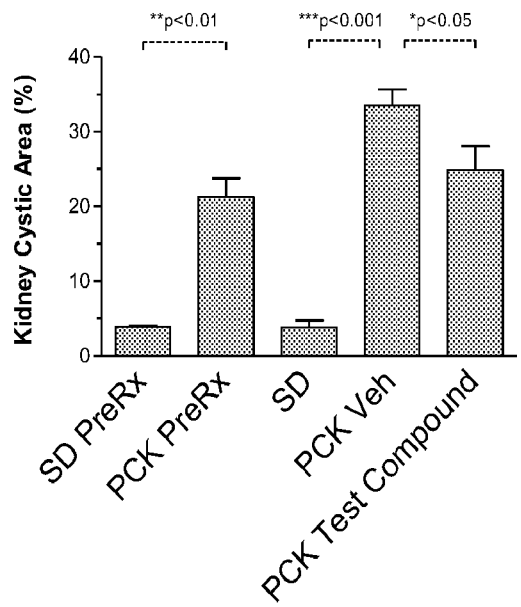
Figure 7:
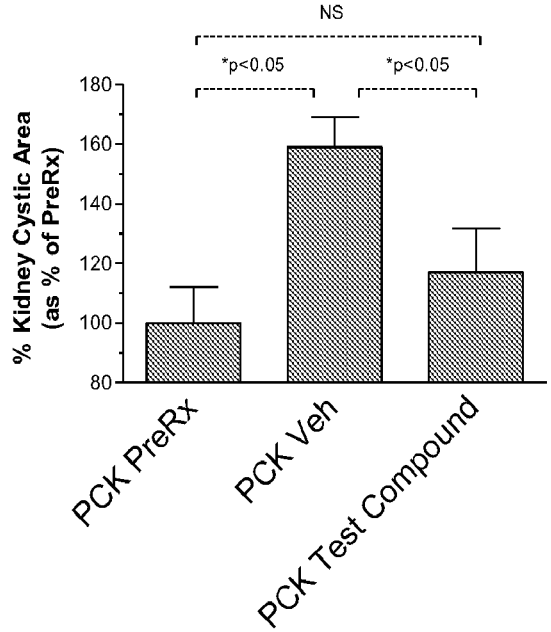
Figure 10:
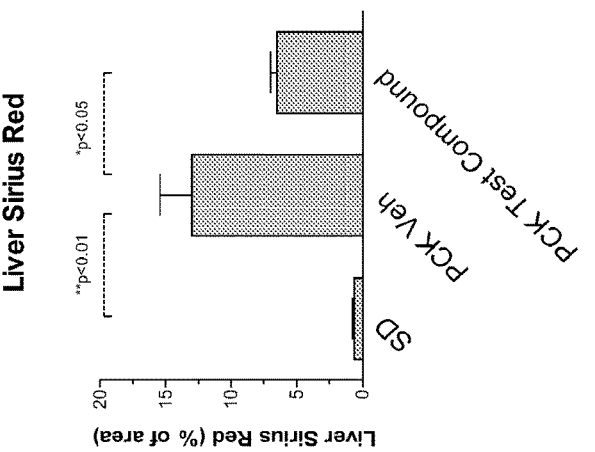
FIG. 10 shows the effect of a compound on liver collagen content as measured by Sirius Red staining in a genetic model of polycystic kidney disease.
Figure 9:
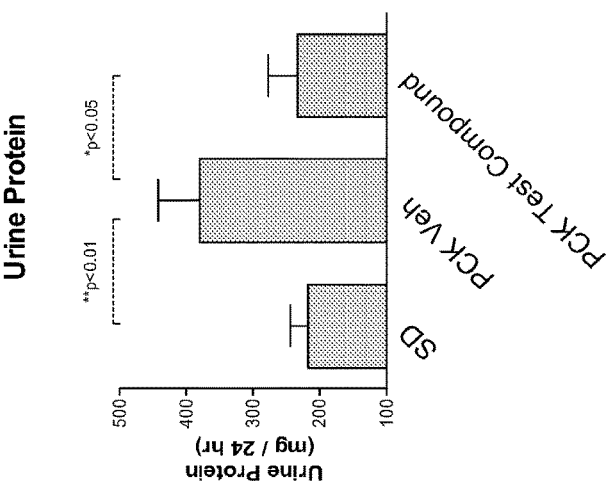
FIG. 9 shows the effect of a compound on urinary protein excretion in a genetic model of polycystic kidney disease.
Figure 8:
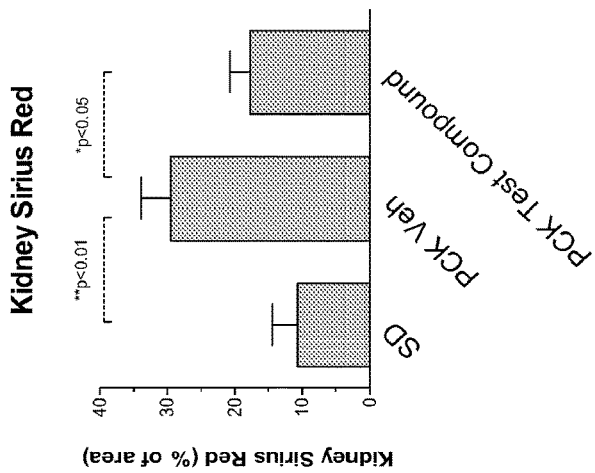
FIG. 8 shows the effect of a compound on kidney collagen content as measured by Sirius Red staining in a genetic model of polycystic kidney disease.

Example 78: Test Compound Improves Renal Function in the Rat Polycystic Kidney Disease Model A compound of the invention was tested in the PCK rat, a model of autosomal recessive polycystic kidney disease (ARPKD). PCK rats (Charles River) carry and autosomal recessive Pkhd1 gene mutation, which results in genetically determined cytogenesis and fibrosis in both kidney and livers. Already at the age of 6 weeks, PCK rats have markedly enlarged kidneys and livers as a result of this cyst formation. PCK animals or Sprague Dawley control animals were dosed with test compound twice a day at 25 mg/kg from the age of 6 weeks to the age of 10 weeks. From week 6 to 10, there is a significant increase in kidney size and the % area of cysts, as determined by quantitative histochemistry of H&E slides. Test compound reduced this increase in kidney weight and the % cystic area from week 6 to week 10 (FIG. 6A) and as expressed as percent of pre-treatment kidney weight, FIG. 6B). While the kidney weight and % cystic area in PCK animals increased from week 6 to 10 in vehicle treated animals by approximately 20% and 60% respectively, kidney weight and kidney cystic area were not significantly increased in animals treated with test compound (FIG. 7A; as percent of pre-treatment cystic area, FIG. 7B). This indicates that the disease progression has been significantly slowed down, a key objective for prospective therapeutics for polycystic kidney disease. Kidney collagen deposition (Sirius Red staining; FIG. 8) and proteinuria (determined in the urine just prior to sacrifice of animals for tissue harvest; FIG. 9) were also ameliorated, indicating that progression to a fibrotic state and deterioration of kidney function are also halted by compound administration. In addition, test compound significantly improves the liver pathology associated with renal dysfunction, as observed e.g. in the increase in liver collagen deposition (hydroxyproline) and Sirius Red staining (FIG. 10). Overall, these observations indicate that aldosterone synthase inhibition has a beneficial effect on both kidney and liver manifestations of disease progression in this model of PKD.

What is claimed is:

1. A compound as described in Formula (I)

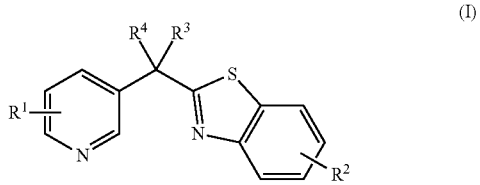

(I)

or a salt or enantiomer, thereof;
wherein $R^1$ is one, two, or three independent halogen, haloalkyl, $NO_2$, CN, $COOR^5$, $SO_2R^5$, $CONR^5R^6$, $SO_2NR^5R^6$, $NR^5R^6$, $OR^5$, alkyl, alkenyl, alkynyl, cycloalkyl, heteroalkyl or aryl;
$R^2$ is one or more independent halogen, haloalkyl, $NO_2$, CN, $COOR^5$, $SO_2R^5$, $CONR^5R^6$, $SO_2NR^5R^6$, $NR^5R^6$, $OR^5$, alkyl, alkenyl, alkynyl, cycloalkyl, heteroalkyl, or aryl;
$R^3$ is alkyl, alkenyl or alkynyl, any of which is further substituted by one or more $R^7$;
$R^4$ is $NR^5R^6$, $SR^5$, or $OR^5$;
$R^5$ and $R^6$ are independently hydrogen, alkyl, aryl or haloalkyl;
$R^7$ is H, halogen, alkyl, haloalkyl, $NO_2$, CN, $COOR^8$, $SO_2R^8$, $CONR^8R^9$, $SO_2NR^8R^9$, $NR^8R^9$, or $OR^8$; and
$R^8$ and $R^9$ are independently hydrogen, alkyl or haloalkyl, and wherein the compound is not benzo[d]thiazol-2-yl (pyridin-3-yl)methanol.

2. The compound of claim 1 wherein each $R^1$ is independently fluoro, chloro, bromo, phenyl, isopropyl, methoxy, ethyloxy, 1-propyloxy or 2-propyloxy.

3. The compound of claim 1 wherein each $R^2$ is independently fluoro, chloro, bromo, cyano, $CONH_2$, nitro, methyl, ethyl, vinyl, trifluoromethyl, diisopropylamino, trifluoromethoxy, trifluoroethoxy, methoxy, phenoxy, (4-fluoro) phenoxy or (4-trifluoromethoxy)phenoxy.

4. The compound of claim 1 wherein $R^2$ represents di-substitution with two same substituents selected from among difluoro, dichloro, dibromo, dimethyl, dimethoxy, ditrifluoromethyl, ditrifluoroethoxy and ditrifluoromethoxy.

5. The compound of claim 1 wherein $R^2$ represents di-substitution with two different substituents selected from fluoro and chloro, fluoro and bromo, fluoro and methoxy, chloro and methoxy, bromo and methoxy, methyl and methoxy, trifluoromethyl and methoxy, trifluoromethoxy and methoxy, fluoro and trifluoromethyl, chloro and trifluoromethyl, bromo and trifluoromethyl, methyl and trifluoromethyl, trifluoromethoxy and trifluoromethyl, fluoro and trifluoromethoxy, chloro and trifluoromethoxy, bromo and trifluoromethoxy, methyl and trifluoromethoxy, trifluoromethyl and trifluoromethoxy, fluoro and trifluoroethoxy, chloro and trifluoroethoxy, bromo and trifluoroethoxy, methyl and trifluoroethoxy, trifluoromethoxy and trifluoroethoxy, and trifluoromethyl and trifluoroethoxy.

6. The compound of claim 1 wherein $R^2$ represents tri-substitution with three same substituents selected from trifluoro, trichloro and tribromo.

7. The compound of claim 1 wherein $R^2$ represents tri-substitution with different substituents selected from difluoro and chloro, difluoro and bromo, difluoro and trifluoromethyl, difluoro and trifluoromethoxy, difluoro and trifluoroethoxy, dichloro and fluoro, dichloro and bromo, dichloro and trifluoromethyl, dichloro and trifluoromethoxy, dichloro and trifluoroethoxy, dibromo and fluoro, dibromo and chloro, dibromo and trifluoromethyl, dibromo and trifluoromethoxy, dibromo and trifluoroethoxy, chloro, bromo and trifluoromethyl, and chloro, bromo and trifluoromethoxy.

8. The compound of claim 1 wherein $R^3$ is methyl, ethyl, 1-propyl, 2-propyl, cyclopropyl, isobutyl or t-butyl.

9. The compound of claim 1 wherein $R^4$ is SH, $NH_2$ or OH.

10. The compound of claim 1 selected from 1-(7-bromobenzo[d]thiazol-2-yl)-1-(4-ethoxypyridin-3-yl)-2-methylpropan-1-ol; 1-(6-bromobenzo[d]thiazol-2-yl)-1-(5-methoxypyridin-3-yl)butan-1-ol; 1-(6-bromobenzo[d]thiazol-2-yl)-1-(5-chloropyridin-3-yl)butan-1-ol; 1-(6-bromobenzo[d]thiazol-2-yl)-1-(5-bromopyridin-3-yl)butan-1-ol; 1-(6-bromobenzo[d]thiazol-2-yl)-1-(5-phenylpyridin-3-yl)butan-1-ol; 1-(5-bromobenzo[d]thiazol-2-yl)-1-(5-methoxypyridin-3-yl)butan-1-ol; 1-(5-(diisopropylamino) benzo[d]thiazol-2-yl)-1-(5-methoxypyridin-3-yl)butan-1-ol; 1-(7-bromobenzo[d]thiazol-2-yl)-1-(5-methoxypyridin-3-yl)butan-1-ol; 1-(6-fluorobenzo[d]thiazol-2-yl)-1-(5-methoxypyridin-3-yl)butan-1-ol; 1-(6-bromobenzo[d]thiazol-2-yl)-1-(6-methoxypyridin-3-yl)butan-1-ol; 1-(7-bromobenzo[d]thiazol-2-yl)-1-(4-methoxypyridin-3-yl) butan-1-ol; 1-(6-bromobenzo[d]thiazol-2-yl)-1-(4-methoxypyridin-3-yl)-2-methylpropan-1-ol; 1-(4-methoxypyridin-3-yl)-1-(6-nitrobenzo[d]thiazol-2-yl)butan-1-ol; 1-(6-bromobenzo[d]thiazol-2-yl)-1-(4-ethoxypyridin-3-yl)butan-1-ol; 1-(7-bromobenzo[d]thiazol-2-yl)-1-(4-ethoxypyridin-3-yl)butan-1-ol; 1-(6-bromobenzo[d]thiazol-2-yl)-1-(4-ethoxypyridin-3-yl)-2-methylpropan-1-ol; 1-(6-bromobenzo[d]thiazol-2-yl)-1-(4-isopropylpyridin-3-yl)-2-methylpropan-1-ol; 1-(7-bromobenzo[d]thiazol-2-yl)-1-(4-isopropylpyridin-3-yl)-2-methylpropan-1-ol; 1-(6-bromobenzo[d]thiazol-2-yl)-1-(4-isopropoxypyridin-3-yl)-2-methylpropan-1-ol; 1-(7-bromobenzo[d]thiazol-2-yl)-1-(4-isopropoxypyridin-3-yl)-2-methylpropan-1-ol; 1-(6-bromobenzo[d]thiazol-2-yl)-1-(4-isopropylpyridin-3-yl) butan-1-ol; 1-(7-bromobenzo[d]thiazol-2-yl)-1-(4-isopropylpyridin-3-yl)butan-1-ol; 1-(6-chlorobenzo[d] thiazol-2-yl)-1-(4-ethoxypyridin-3-yl)butan-1-ol; 1-(4-ethoxypyridin-3-yl)-1-(6-nitrobenzo[d]thiazol-2-yl)butan-1-ol; 1-(4-ethoxypyridin-3-yl)-1-(6-fluorobenzo[d]thiazol-2-yl)butan-1-ol; 1-(7-chlorobenzo[d]thiazol-2-yl)-1-(4-ethoxypyridin-3-yl)butan-1-ol; 1-(4,7-difluorobenzo[d] thiazol-2-yl)-1-(4-ethoxypyridin-3-yl)butan-1-ol; 1-(4-ethoxypyridin-3-yl)-1-(7-methoxybenzo[d]thiazol-2-yl) butan-1-ol; 1-(4-ethoxypyridin-3-yl)-1-(6-(trifluoromethyl) benzo[d]thiazol-2-yl)butan-1-ol; 1-(4-ethoxypyridin-3-yl)-1-(6-(trifluoromethoxy)benzo[d]thiazol-2-yl)butan-1-ol; 1-(4-ethoxypyridin-3-yl)-1-(7-(trifluoromethyl)benzo[d]thiazol-2-yl)butan-1-ol; 1-(4-ethoxypyridin-3-yl)-1-(6-methoxybenzo[d]thiazol-2-yl)butan-1-ol; 1-(4-isopropoxypyridin-3-yl)-1-(6-(trifluoromethoxy)benzo[d]thiazol-2-yl)butan-1-ol; 1-(5,6-dichlorobenzo[d]thiazol-2-yl)-1-(4-ethoxypyridin-3-yl)butan-1-ol; 1-(4-propoxypyridin-3-yl)-1-(6-(trifluoromethoxy)benzo[d]thiazol-2-yl)butan-1-ol; 1-(7-bromobenzo[d]thiazol-2-yl)-1-(4-methoxypyridin-3-yl)-2-methylpropan-1-ol; 1-(4-ethoxypyridin-3-yl)-1-(6-(4-(methoxy)phenoxy)benzo[d]thiazol-2-yl)butan-1-ol; 1-(4-ethoxypyridin-3-yl)-1-(6-(4-fluorophenoxy)benzo[d]thiazol-2-yl)butan-1-ol; 1-(5-bromo-6-(trifluoromethoxy)benzo[d]thiazol-2-yl)-1-(4-ethoxypyridin-3-yl)butan-1-ol; 1-(7-bromo-6-(trifluoromethoxy)benzo[d]thiazol-2-yl)-1-(4-ethoxypyridin-3-yl)butan-1-ol; 1-(5-chloro-6-(trifluoromethoxy)benzo[d]thiazol-2-yl)-1-(4-ethoxypyridin-3-yl)butan-1-ol; 1-(7-chloro-6-(trifluoromethoxy)benzo[d]thiazol-2-yl)-1-(4-ethoxypyridin-3-yl)butan-1-ol; 1-(4-ethoxypyridin-3-yl)-1-(5-methyl-6-(trifluoromethoxy)benzo[d]thiazol-2-yl)butan-1-ol; 1-(4-ethoxypyridin-3-yl)-1-(7-methyl-6-(trifluoromethoxy)benzo[d]thiazol-2-yl)butan-1-ol; (R)-1-(4-ethoxypyridin-3-yl)-1-(6-(trifluoromethoxy)-7-(trifluoromethyl)benzo[d]thiazol-2-yl)butan-1-ol; (R)-1-(6-bromobenzo[d]thiazol-2-yl)-1-(4-propoxypyridin-3-yl)butan-1-ol; (S)-1-(4-ethoxypyridin-3-yl)-1-(6-(trifluoromethoxy)-7-(trifluoromethyl)benzo[d]thiazol-2-yl)butan-1-ol; (S)-1-(6-bromobenzo[d]thiazol-2-yl)-1-(4-propoxypyridin-3-yl)butan-1-ol; 1-(4-ethoxypyridin-3-yl)-1-(6-(trifluoromethoxy)-5-(trifluoromethyl)benzo[d]thiazol-2-yl)butan-1-ol; 1-(4-ethoxypyridin-3-yl)-1-(7-methoxy-6-(trifluoromethoxy)benzo[d]thiazol-2-yl)butan-1-ol; 1-(4-propoxypyridin-3-yl)-1-(6-(trifluoromethoxy)-5-(trifluoromethyl)benzo[d]thiazol-2-yl)butan-1-ol; 1-(4-propoxypyridin-3-yl)-1-(6-(trifluoromethyl)benzo[d]thiazol-2-yl)butan-1-ol; 1-(5,6-bis(trifluoromethoxy)benzo[d]thiazol-2-yl)-1-(4-ethoxypyridin-3-yl)butan-1-ol; 1-(5-bromo-6-(trifluoromethoxy)benzo[d]thiazol-2-yl)-1-(4-propoxypyridin-3-yl)butan-1-ol; 1-(6,7-bis(trifluoromethoxy)benzo[d]thiazol-2-yl)-1-(4-ethoxypyridin-3-yl)butan-1-ol; 1-(6-bromobenzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-ethoxy-5-methoxypyridin-3-yl)butan-1-ol; 1-(7-bromo-6-(trifluoromethoxy)benzo[d]thiazol-2-yl)-1-(4-propoxypyridin-3-yl)butan-1-ol; 1-(7-bromobenzo[d]thiazol-2-yl)-1-(4-ethoxy-5-methoxypyridin-3-yl)butan-1-ol; 1-(4-ethoxypyridin-3-yl)-1-(5-fluoro-6-(trifluoromethoxy)benzo[d]thiazol-2-yl)butan-1-ol; 1-(5-chloro-6-(trifluoromethoxy)benzo[d]thiazol-2-yl)-1-(4-propoxypyridin-3-yl)butan-1-ol; 1-(7-chloro-6-(trifluoromethoxy)benzo[d]thiazol-2-yl)-1-(4-propoxypyridin-3-yl)butan-1-ol; 1-(6-bromo-5,7-dichlorobenzo[d]thiazol-2-yl)-1-(4-propoxypyridin-3-yl)butan-1-ol; 1-(4-propoxypyridin-3-yl)-1-(5,6,7-trichlorobenzo[d]thiazol-2-yl)butan-1-ol; 1-(5,7-dichloro-6-(2,2,2-trifluoroethoxy)benzo[d]thiazol-2-yl)-1-(4-propoxypyridin-3-yl)butan-1-ol; 1-(7-chloro-6-(2,2,2-trifluoroethoxy)benzo[d]thiazol-2-yl)-1-(4-propoxypyridin-3-yl)butan-1-ol; 1-(5-chloro-6-(2,2,2-trifluoroethoxy)benzo[d]thiazol-2-yl)-1-(4-ethoxypyridin-3-yl)butan-1-ol; 1-(5,7-difluoro-6-(trifluoromethoxy)benzo[d]thiazol-2-yl)-1-(4-ethoxypyridin-3-yl)butan-1-ol; 1-(5,7-dichloro-6-(trifluoromethoxy)benzo[d]thiazol-2-yl)-1-(4-ethoxypyridin-3-yl)butan-1-ol; 1-(6-bromobenzo[d]thiazol-2-yl)-1-(4-methoxypyridin-3-yl)butan-1-ol; 1-(7-bromobenzo[d]thiazol-2-yl)-1-(4-methoxypyridin-3-yl)-2-methylpropan-1-ol; 1-(6-cyanobenzo[d]thiazol-2-yl)-1-(4-ethoxypyridin-3-yl)butan-1-ol; 2-(1-(4-ethoxypyridin-3-yl)-1-hydroxybutyl)benzo[d]thiazole-6-carboxamide; and 1-(7-bromobenzo[d]thiazol-2-yl)-1-(4-propoxypyridin-3-yl)butan-1-ol.

11. A pharmaceutical composition comprising a compound of claim 1 and a pharmaceutically acceptable carrier, diluent or excipient.

\* \* \* \* \*